United States Patent
Faaren et al.

(10) Patent No.: US 10,494,660 B2
(45) Date of Patent: Dec. 3, 2019

(54) BLOOD SAMPLE ASSAY METHOD

(71) Applicant: AXIS-SHIELD AS, Oslo (NO)

(72) Inventors: Arne Ludvig Faaren, Oslo (NO); Frank Frantzen, Oslo (NO); Arne Kristian Nordhei, Oslo (NO); Erling Sundrehagen, Oslo (NO); Lars Ørning, Oslo (NO)

(73) Assignee: AXIS-SHIELD AS, Oslo (NO)

( * ) Notice: Subject to any disclaimer, the term of this patent is extended or adjusted under 35 U.S.C. 154(b) by 0 days.

(21) Appl. No.: 15/629,672

(22) Filed: Jun. 21, 2017

(65) Prior Publication Data
US 2017/0349933 A1 Dec. 7, 2017

Related U.S. Application Data

(62) Division of application No. 14/357,561, filed as application No. PCT/EP2012/072336 on Nov. 9, 2012, now Pat. No. 9,695,464.

(30) Foreign Application Priority Data

Nov. 11, 2011 (GB) .................................. 1119515.3
Jan. 24, 2012 (GB) .................................. 1201154
Jan. 25, 2012 (GB) .................................. 1201245.6

(51) Int. Cl.
C12Q 1/60 (2006.01)
C12Q 1/61 (2006.01)
G01N 33/92 (2006.01)

(52) U.S. Cl.
CPC ................. C12Q 1/60 (2013.01); C12Q 1/61 (2013.01); G01N 33/92 (2013.01)

(58) Field of Classification Search
CPC .................................... C12Q 1/60; C12Q 1/26
See application file for complete search history.

(56) References Cited

U.S. PATENT DOCUMENTS

| 4,828,986 A | 5/1989 | Smith et al. |
| 5,118,613 A | 6/1992 | McGowan |

(Continued)

FOREIGN PATENT DOCUMENTS

| EP | 1148142 A1 | 10/2001 |
| EP | 1164376 B1 | 12/2001 |

(Continued)

OTHER PUBLICATIONS

Extended Search Report related EP 18193553, dated Oct. 15, 2018, 8 pages.

(Continued)

Primary Examiner — Rosanne Kosson
(74) Attorney, Agent, or Firm — Casimir Jones S.C.; Thomas Isenbarger

(57) ABSTRACT

The invention provides an enzymatic method for measuring the concentration of one or more analytes in the plasma portion of a blood derived sample, containing a first and a second component, where said second component interferes with the measurement of said first component. The method includes: i) diluting the sample with a reagent mixture; ii) substantially removing blood cells; iii) using a reagent which serves to temporarily prevent reaction of the second component, to generate a blocked second component; iv) causing the selective reaction of a constituent of each analyte to directly or indirectly generate detectable reaction products, where one of the analytes is the first component; v) monitoring the detectable reaction product or products; vi) relating an amount of the detectable product or products and/or a rate of formation of the detectable product or products to the concentration of each analyte, where the concentration of at least the first component is related to a corresponding detectable reaction product by means of estimating an un-measurable (fictive) endpoint. Step iii) may (Continued)

be carried out at any stage up to and including step iv) but before steps v) or vi). The reagent of step iii) may be applied to the sample separately or may be included in a reagent mixture during steps i) or iv). A corresponding kit is also provided.

24 Claims, 8 Drawing Sheets

(56) References Cited

U.S. PATENT DOCUMENTS

| | | | |
|---|---|---|---|
| 5,691,159 | A | 11/1997 | Miyauchi et al. |
| 5,773,304 | A | 6/1998 | Hino et al. |
| 5,807,696 | A | 9/1998 | Miyauchi et al. |
| 5,888,827 | A | 3/1999 | Kayahara et al. |
| 5,925,534 | A | 7/1999 | Miki et al. |
| 6,057,118 | A | 5/2000 | Nakamura et al. |
| 6,162,607 | A | 12/2000 | Miki et al. |
| 6,194,164 | B1 | 2/2001 | Matsui et al. |
| 6,479,249 | B2 | 11/2002 | Matsui et al. |
| 6,811,994 | B1 | 11/2004 | Miyauchi et al. |
| 6,818,414 | B1 | 11/2004 | Nakamura et al. |
| 6,893,832 | B2 | 5/2005 | Matsui et al. |
| 6,986,998 | B2 | 1/2006 | Kishi et al. |
| 7,202,047 | B2 | 4/2007 | Miyauchi |
| 7,208,287 | B2 | 4/2007 | Kishi et al. |
| 8,192,926 | B2 | 6/2012 | Debad et al. |
| 9,695,464 | B2 | 7/2017 | Faaren et al. |
| 2004/0235182 | A1 | 11/2004 | Jones |
| 2005/0208609 | A1 | 9/2005 | Jones et al. |
| 2006/0019404 | A1 | 1/2006 | Blatt |
| 2007/0161068 | A1 | 7/2007 | Miyauchi |
| 2007/0207515 | A1 | 9/2007 | Matsumoto et al. |
| 2009/0215097 | A1 | 8/2009 | Itai et al. |
| 2009/0226944 | A1 | 9/2009 | Katayama et al. |
| 2012/0065898 | A1 | 3/2012 | Kamihara et al. |
| 2012/0107850 | A1 | 5/2012 | Maruyama et al. |

FOREIGN PATENT DOCUMENTS

| | | |
|---|---|---|
| EP | 1329724 A2 | 7/2003 |
| EP | 1413883 A1 | 4/2004 |
| EP | 1715060 A1 | 10/2006 |
| JP | S 58-60259 A | 4/1983 |
| JP | 0 6194313 A2 | 7/1994 |
| JP | H 9-96637 A | 4/1997 |
| JP | 2009-39015 A | 2/2009 |
| WO | WO 1997040376 | 10/1997 |
| WO | 2000060112 A1 | 10/2000 |
| WO | 2006027283 A1 | 3/2006 |
| WO | WO 2006027283 A1 | 3/2006 |
| WO | WO 2007007392 A1 | 1/2007 |
| WO | WO 2008114060 A1 | 9/2008 |
| WO | 2009081140 A1 | 7/2009 |
| WO | WO 2013068572 A1 | 5/2013 |

OTHER PUBLICATIONS

Japanese Office Action of related JP Application No. 2017-018645, dated May 29, 2018, 5 pages.
Japanese Office Action of related JP Application No. 2014-540495, dated May 15, 2018.
HDL-Cholestorel Kit Wako L-Type HDL-C, Feb. 2007, First Edition (Newly cited document; Document showing a technical level) 5 pages.
Kvam, Catrine, et al. "Development and performance of an albumin-creatinine ratio assay on the Afinion AS100 analyzer." Point of Care 8.1 (2009): 16-20.
International Search Report for PCT/EP/2012/072336, dated Jun. 12, 2013 (Jun. 12, 2013); the entire document.
Sugiuchi H et al: "Homogeneous Assay for Measuring Low-Density Lipoprotein Cholesterol in Serum With Triblock Copolymer and Alpha-Cyclodextrin Sulfate", Clinical Chemistry, 2 American Association for Clinical Chemistry, Washington, DC, vol. 44, No. 3, Jan. 1, 1998 (Jan. 1, 1998), pp. 522-531, XP002920066, ISSN: 0009-9147 the whole document.
Pesce et al: "Enzymatic rate method for measuring cholesterol in serum.", Clinical Chemistry, vol. 22, No. 12, Dec. 1, 1976 (Dec. 1, 1976), pp. 2042-2045, XP055054989, ISSN: 0009-9147 figures 1,2.
Wako Pure Chemical Industries, Ltd. "New Wako HDL-C-M Reagent" Sep. 10, 2007, 19 pages.
Fujifilm Wako Pure Chemical Corporation "Product List" Retrieved Mar. 19, 2019, from http://wako-chem.co.jp/diagnostic/product-list.htm, 1 page.
Barlow et al., "Hill coefficients and the logistic equation," Trends in Pharmacological Sciences, 1989; 10(11):440-441.
Prinz, "Hill coefficients, dose-response curves and allosteric mechanisms," Journal of Chemical Biology, 2010; 3 (1):37-44.
Price CP, "Point of care testing," BMJ. May 26, 2001;322(7297):1285-8.
Lopes-Virella et al., "Cholesterol determination in high-density lipoproteins separated by three different methods," Clin Chem. May 1977;23(5):882-4.
Finley et al., "Cholesterol in high-density lipoprotein: use of Mg2+/dextran sulfate in its enzymic measurement," Clin Chem. Jun. 1978;24(6):931-3.
Kimberly et al., "Selection, validation, standardization, and performance of a designated comparison method for HDL-cholesterol for use in the cholesterol reference method laboratory network," Clin Chem. Oct. 1999;45(10):1803-12.
Conlin D et al., "Quantitative determination of high-density lipoprotein cholesterol by agarose gel electrophoresis," Clin Chem. Nov. 1979;25(11):1965-9.
Usui et al., "Assessment of between-instrument variations in a HPLC method for serum lipoproteins and its traceability to reference methods for total cholesterol and HDL-cholesterol", Clin Chem. Jan. 2000;46(1):63-72.
Friedewald et al., "Estimation of the concentration of low-density lipoprotein cholesterol in plasma, without use of the preparative ultracentrifuge," Clin Chem. Jun. 1972;18(6):499-502.
Mora et al., "Comparison of LDL cholesterol concentrations by Friedewald calculation and direct measurement in relation to cardiovascular events in 27,331 women," Clin Chem. May 2009;55(5):888-94.
Havel et al., "The distribution and chemical composition of ultracentrifugally separated lipoproteins in human serum," J Clin Invest. Sep. 1955;34(9):1345-53.
van Deventer et al., "Non-HDL cholesterol shows improved accuracy for cardiovascular risk score classification compared to direct or calculated LDL cholesterol in a dyslipidemic population," Clin Chem. Mar. 2011;57(3):490-501.
Sniderman et al., "A meta-analysis of low-density lipoprotein cholesterol, non-high-density lipoprotein cholesterol, and apolipoprotein B as markers of cardiovascular risk," Circ Cardiovasc Qual Outcomes. May 2011;4(3):337-45.
Sniderman et al., "Why is non-high-density lipoprotein cholesterol a better marker of the risk of vascular disease than low-density lipoprotein cholesterol?" J Clin Lipidol. May-Jun. 2010;4(3):152-5.
London et al., "Progress curve algorithm for calculating enzyme activities from kinetic assay spectrophotometric measurements," Anal Chem. Oct. 1977;49(12):1716-9.
Hainline A et al., Manual of laboratory operations, lipid and lipoprotein analysis, 2nd ed Bethesda, MD.: US Department of Health and Human Service, 1982:151.
Vikari "Precipitation of plasma lipoproteins by PEG-6000 and its evaluation with electrophoresis and ultracentrifugation." Scand J Clin Lab Invest. May 1976;36(3):265-8.

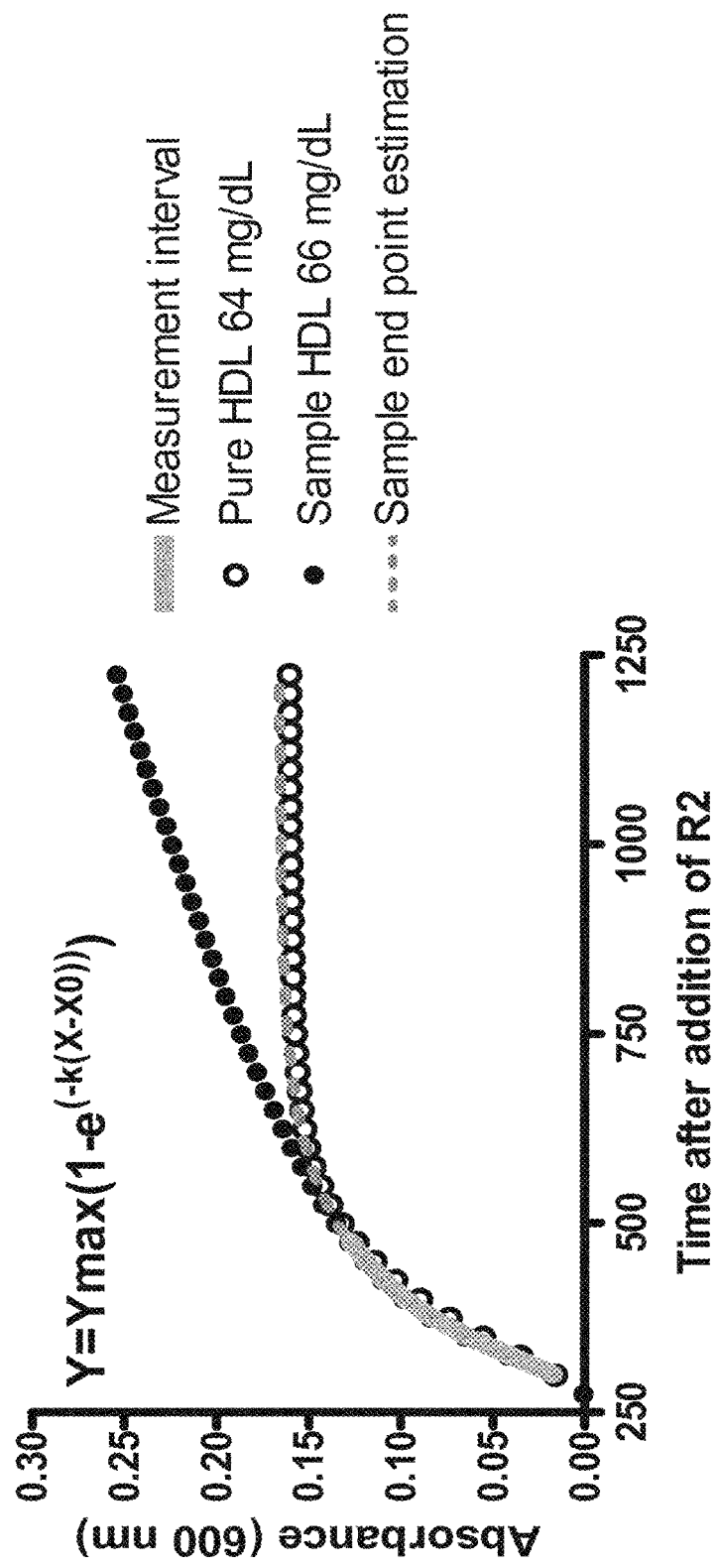
Fig. 1. Estimation of a fictive end measurement of HDL associated cholesterol in the presence of cholesterol associated with non-HDL.

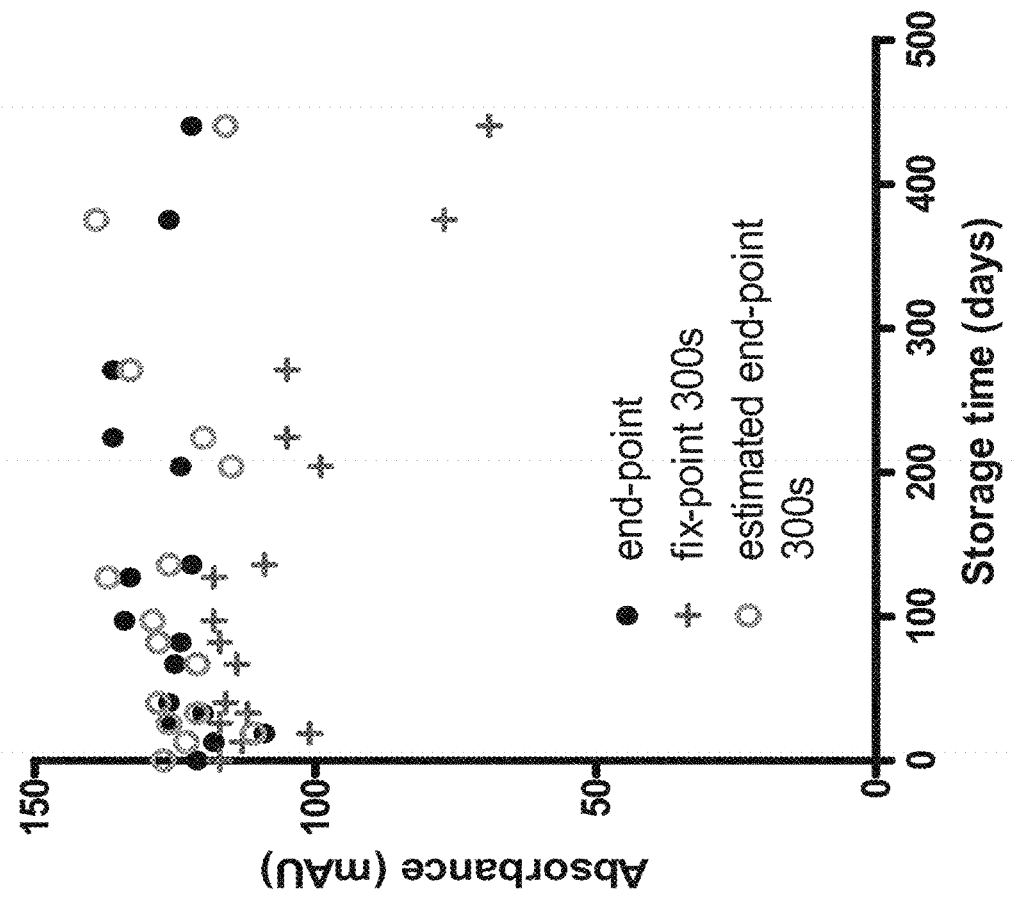
Fig. 2. Comparison of end-point, fix-point and estimated end-point measurements in the Roche triglyceride assay. Long term stability at 25°C

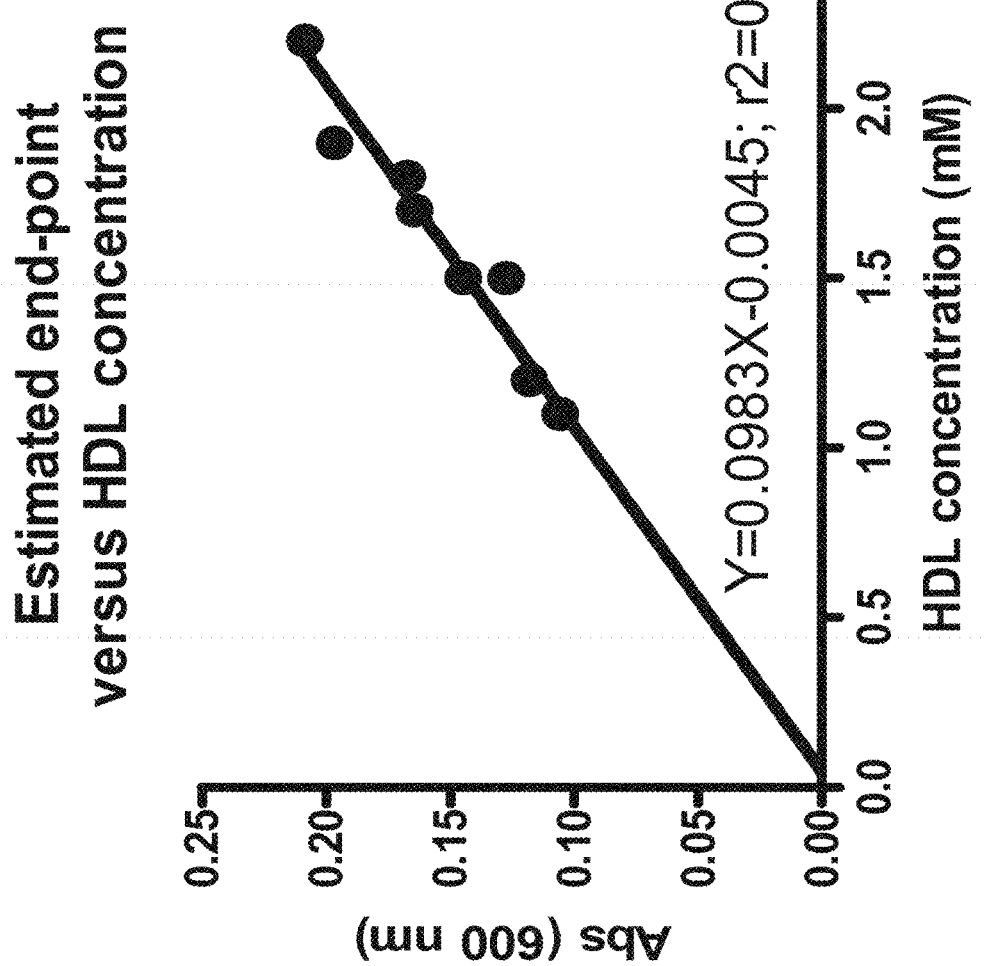
Fig.3 End-point estimation of the Roche HDL assay

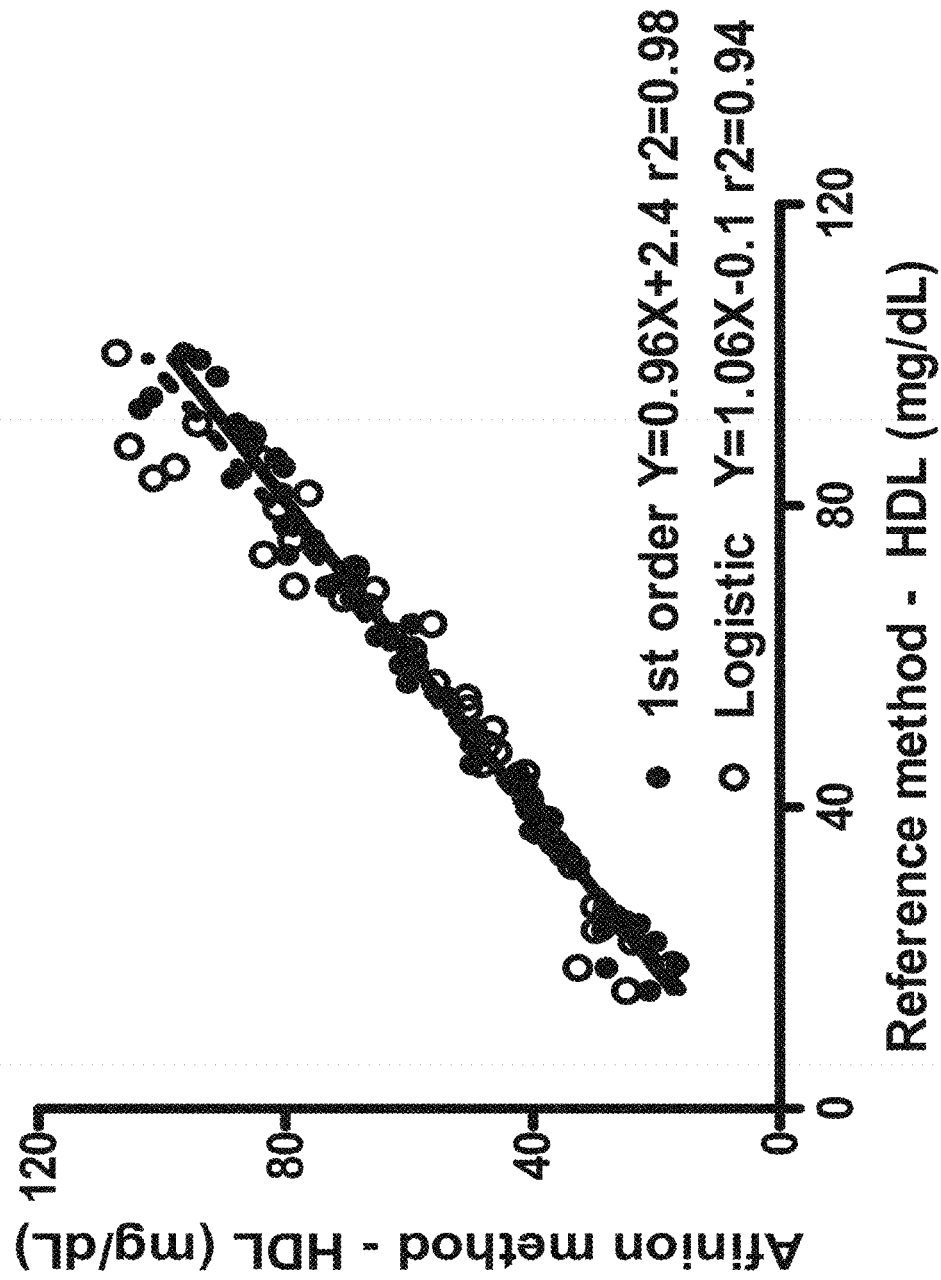
Fig.4 - Comparison of Afinion "Point of Care" method using end-point estimation to clinical laboratory method.

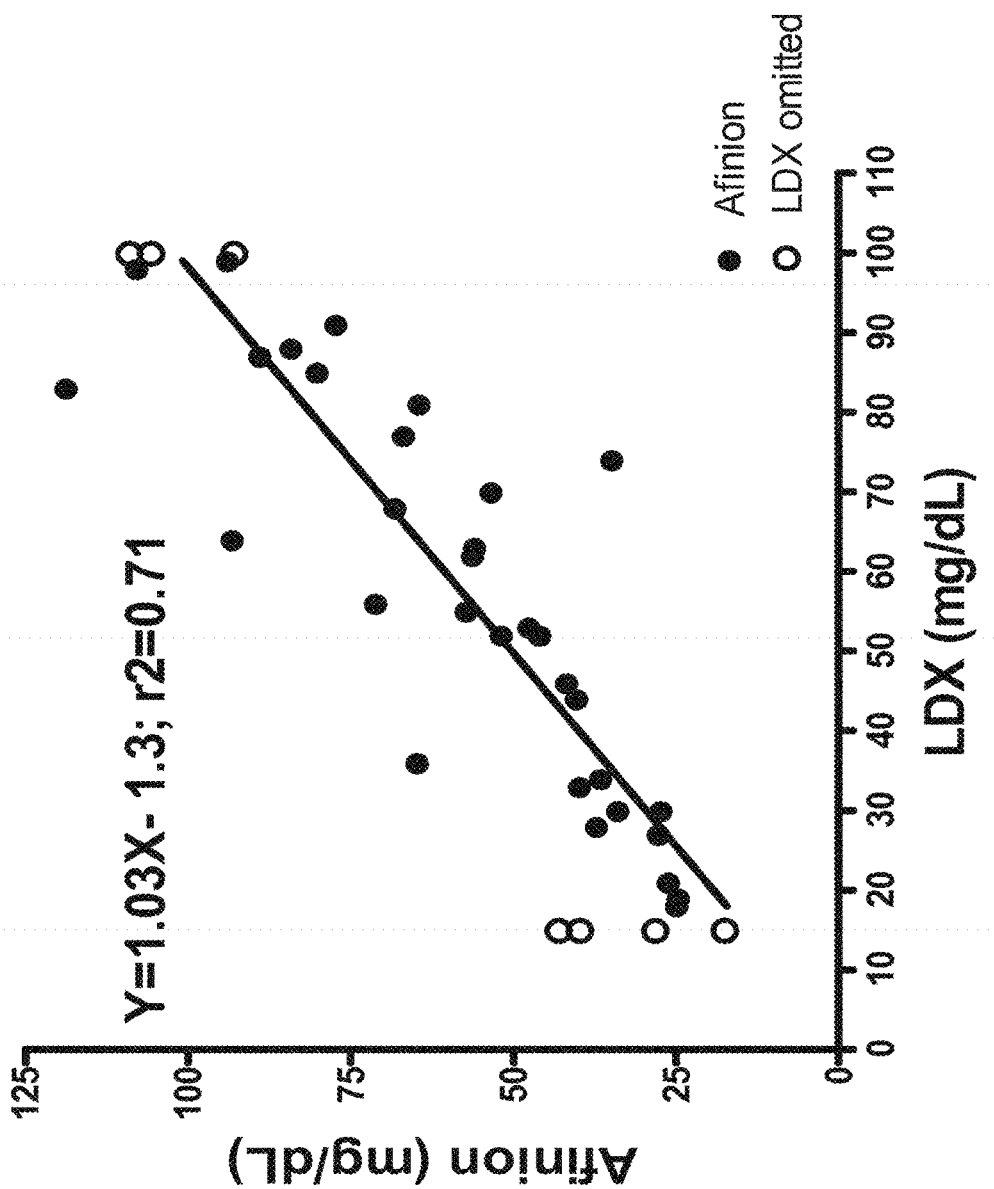

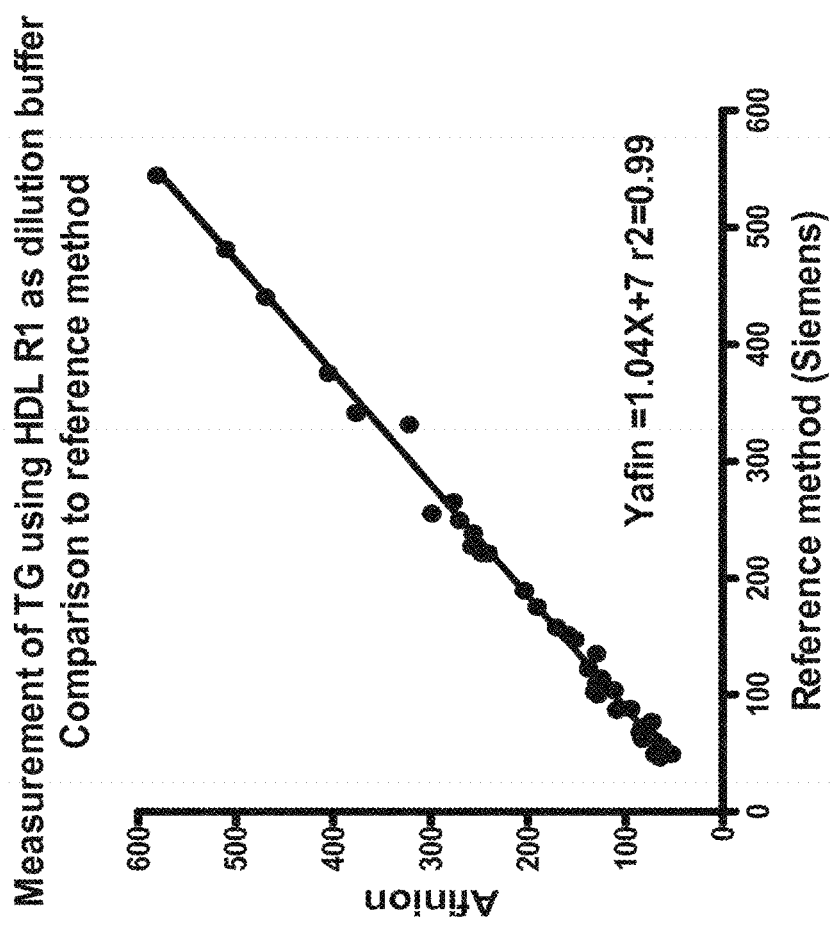
Figure 6 use of a dilution buffer containing a nonHDL blocking reagent

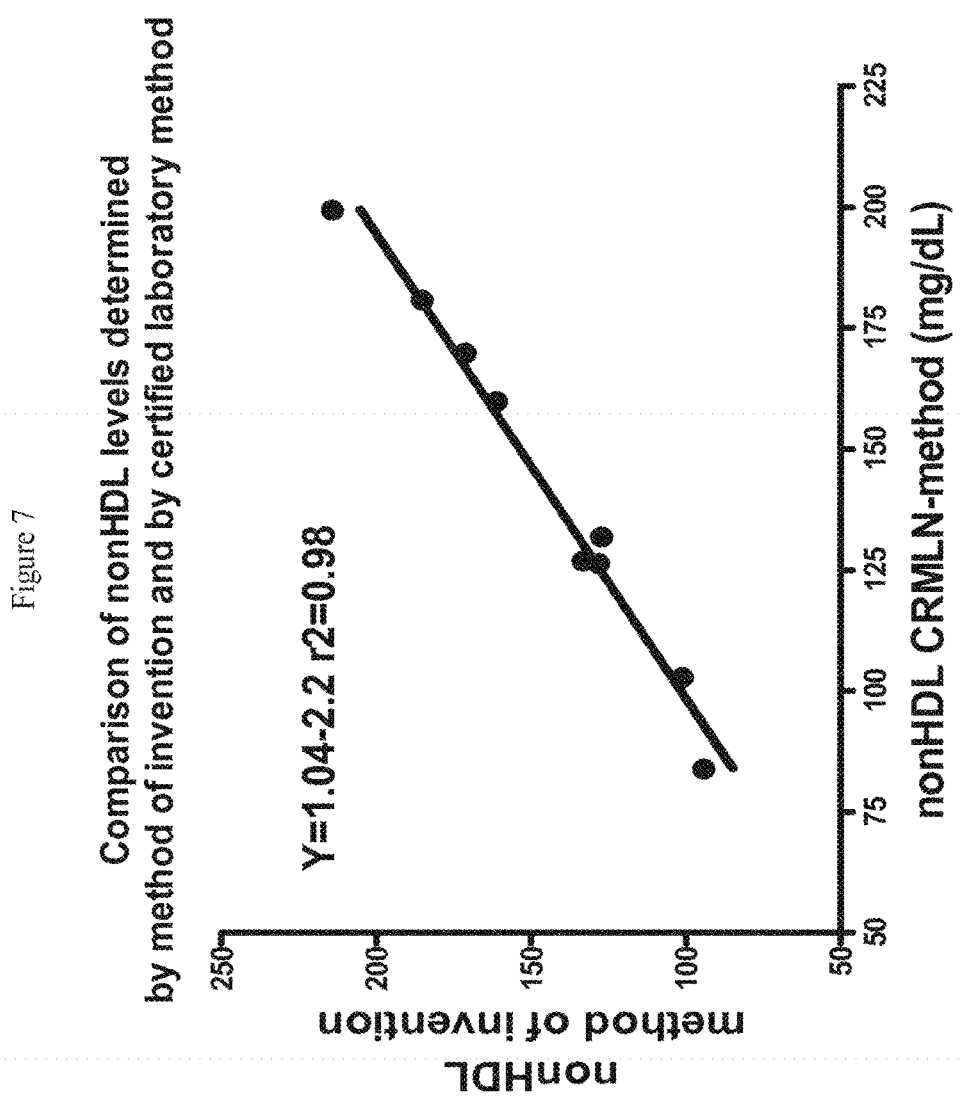

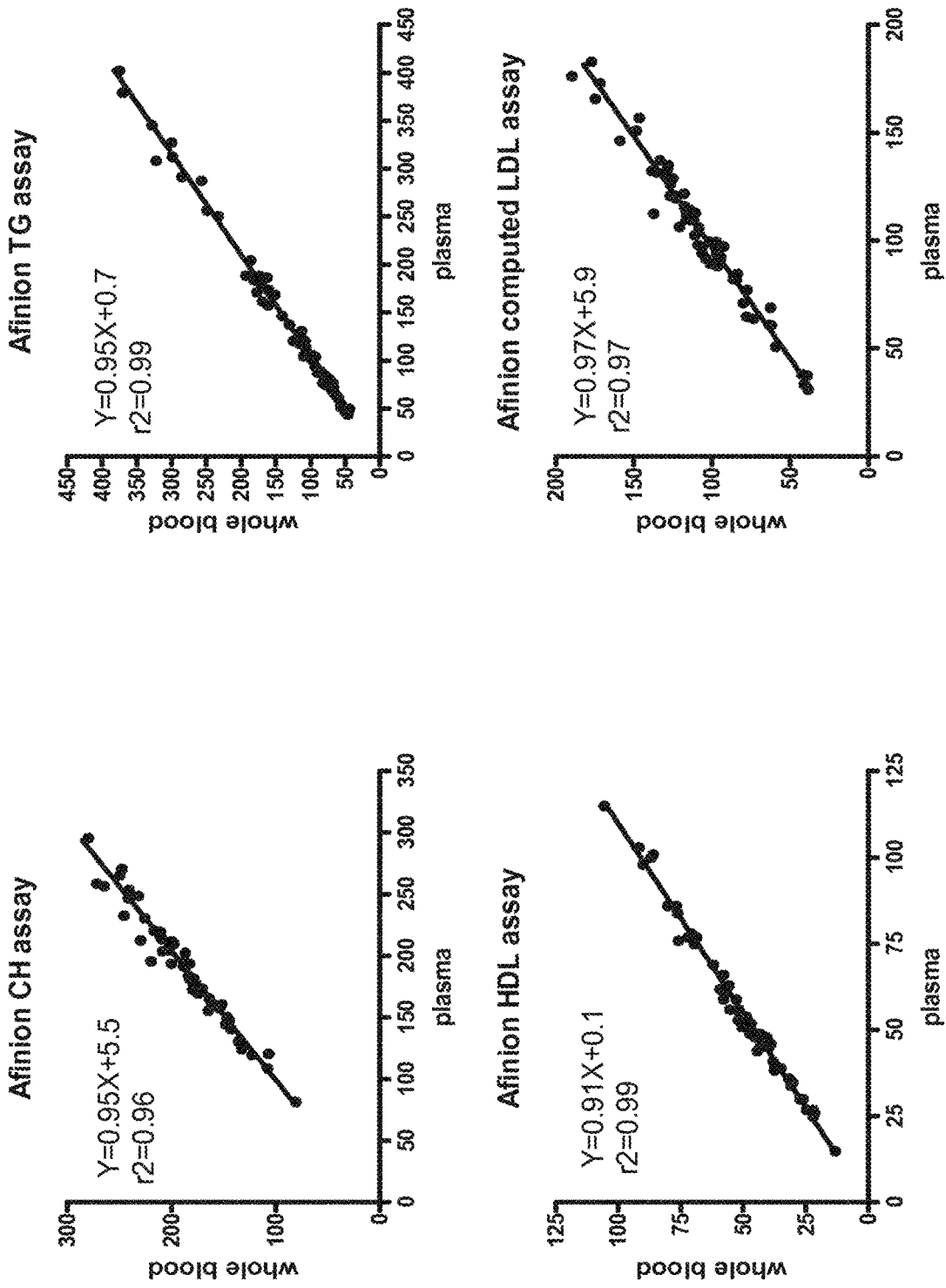
Figure 8 - comparison of profiles from whole-blood with those from plasma

BLOOD SAMPLE ASSAY METHOD

CLAIM FOR PRIORITY

This application is a divisional application which claims priority to U.S. application Ser. No. 14/357,561, filed on May 9, 2017, which claims priority under 35 USC 371 to International Application No. PCT/EP2012/072336, filed on Nov. 9, 2012, which claims priority to British Patent Application No. 1119515.3, filed on Nov. 11, 2011; British Patent Application No. 1201154.0, filed on Jan. 24, 2012; and British Patent Application No. 1201245.6, filed on Jan. 25, 2012, each of which is hereby incorporated by reference in its entirety.

FIELD OF THE INVENTION

The present invention relates to the measurement of components such as lipid components in a cell-containing blood sample such as a whole blood sample. Specifically, the invention relates to the measurement of plasma lipid components such as cholesterol and triglyceride associated with specific classes of lipoprotein, particularly by means of enzymatic assays. Most particularly, the invention relates to assays such as diagnostic, prognostic and risk determining assays for use in automated methods conducted on a "point-of-care" apparatus.

BACKGROUND TO THE INVENTION

The measurement of components in body samples is a common feature of clinical assessments. Many diagnoses can be made or confirmed, the state or progress of a disease elucidated, or the risk of many conditions can be assessed, from the concentration of a particular analyte in a body sample, or from the profile of concentrations of several components. The increasing number of known correlations between disease states and the concentrations of one or more analytes makes sample analysis for both single and multiple analytes an increasingly valuable tool. There is thus a correspondingly increasing pressure on clinical laboratories to analyse ever larger numbers of samples increasingly quickly. To satisfy this, there is a need for assays which are quicker, higher throughput, simpler and/or more completely automated.

There is a growing demand for assays to be carried out at the "point of care". A demand that is increasing with the ongoing transfer of chronic diseases to primary care. This is beneficial for the patient, who receives immediate advice and is left with less uncertainty. It has also been shown that "near patient" testing improves patient compliance, adherence to treatment and therapeutic control (Price. (2001) BMJ 332:1285-8). It is also beneficial for the medical practitioner, who can potentially avoid the need for a multiple appointments and can be more certain of her judgements.

Point of care assays are exceptionally demanding in terms of the need for simple manipulation and rapid results. If an assay takes more than a few minutes then much of the advantage of conducting it at the point-of-care is lost. Furthermore, although the staff conducting such assays are likely to be healthcare professionals, they are not analytical specialists and will not have access to multiple instruments. It is therefore necessary that such assays be designed to rely on the minimum of sample handling. For this reason, and for reasons of time, personnel resources and cost, it is often of great advantage for a plurality of different analyte levels to be determined in a single operation using a single sample on a single analytical instrument and a single test device. This avoids the costly and time consuming-need for extended sample manipulations, multiple test devices or multiple analytical instruments.

One particular problem with point-of-care methods is that they can seldom accommodate calibration. This is of special concern in enzyme based assay methods since enzymes by their nature are sensitive to inactivation during storage.

A common way to avoid the problem of unknown enzyme activity is to determine the end-point of the enzyme reaction. The amount of end-product formed will depend solely on the amount of analyte present at the start of the reaction, providing that there is sufficient reagent to convert all analyte into product and sufficient time is provided for full conversion. As long as there is sufficient active enzyme to catalyse the reaction, the activity of that enzyme will determine only the rate of reaction and not the end-point. However, this approach requires either a great excess of enzyme, which increases cost and/or requires a sufficiently long assay time, which increases total assay time. This is of particular concern to point-of-care assays, which typically should be completed in 5-10 minutes.

Of special concern are enzymatic reactions which do not produce a measurable end-point. Such situations include consecutive reactions where the next reaction begins before the preceding reaction has reached an end-point or where parallel reactions occur. Similarly, where one component is reacted in the presence of a blocked second component that would react in the absence of the "block" then an end-point can only be reached if the blocking is "permanent", such as by covalent reaction. However, many blocking reagents have only a temporary effect and thus the end point of the reaction of a first component cannot be reached if the second component becomes to any extent "unblocked" during the period required for that end-point to be reached. Typical examples are the measurement of lipid components of specific lipoproteins, e.g. cholesterol associated with high-density lipoprotein. Blocking of lipoprotein components is generally a temporary, kinetic, type of block. This makes typical end-point assays difficult or impossible and other methods such as assays based on fixed-point measurements must be used. These cases are rate-dependent and thus require either fully stable reagents (typically dry reagents), or inclusion of calibrators, to allow compensation for long-term reagent decay. Dried reagents have the disadvantage that they are prone to errors upon reconstitution, often require lengthy reconstitution times, suffer from activity losses during the drying process and, in particular in case of in-device dried reagents, add to the cost of production. Calibrators are frequently not compatible with point-of-care assays.

The structure of a lipoprotein typically has the lipid constituent bound tightly into an inaccessible mass with the protein constituent. Enzymatic reactions will thus generally not affect lipids bound tightly into lipoproteins, or will do so at a very slow rate. Reagent mixtures for the enzymatic reaction of lipids from within lipoproteins thus also typically contain reagents, such as surfactants, that help to "unlock" the lipoprotein and expose the lipid constituents to the action of the enzyme(s). "Blocking" of a lipoprotein component is thus often the stabilisation of that component against the action of such surfactants so that the "blocked" component is not made available for enzymatic reaction. However, over time, the enzymes and/or the surfactants in the reaction mixture will generally begin to cause some degradation of even a blocked lipoprotein component. This then causes a catastrophic effect where the action of the reagents begins to open the lipoprotein structure, which then becomes more reactive and thus more open and so forth. Correspondingly, a "blocked" lipid component can be relied upon to take no measurable part in a reaction for a certain length of time (such as a few hundred seconds) before rapidly and increasingly losing its "block" and causing significant interference. Such temporary blocks cannot be used in an end-point reaction because the block will be broken down before the end point can be reached and thus the result will not represent the desired component.

It is also of note that where the component which it is desirable to measure contains a relatively small portion of the total amount of a particular type of lipid (e.g. less than 30% of the total in a typical healthy patient) then it is particularly important that when the remainder is "blocked", the assay is carried out before this blocking can become significantly undone. This is because a relatively small unblocking of a large component will have a significant effect upon the result when the smaller component is analysed.

In view of the above, current point-of-care instruments cannot use liquid reagents because they cannot include a calibrator and cannot use end-point analysis because the endpoint is unreachable or unmeasurable. The only solution that has been available for manufacturers of such instruments has thus been the use of stabilised reagents, typically in dried form. This however has its own disadvantages. Not only are dried reagents more expensive but their reconstitution is both time consuming and potentially unreliable. Machines using such dried reagents thus tend to have a higher proportion of anomalous results than expected, probably because of the occasional failure of the enzymatic reagent to be fully reconstituted. A method that allowed reactions having no measurable end-point to be used reliably with solution reagents in the absence of calibrators would thus be of considerable value.

The most common clinical samples taken for assay are fluids, particularly blood and urine, since these are relatively easy to take and to manipulate. In blood, it is typically the content of the fluid plasma which is analysed. Some of the most common and clinically important measurements made on blood-derived samples relate to the plasma lipid contents. The predominant lipids present in blood plasma are phospholipids(PL), triglycerides (TG), and cholesterol (CH). Of these TG and CH are of particular diagnostic interest because of their association with cardiovascular disease, which in turn is one of the most prevalent diseases in the developed world.

Lipids are by their very nature water insoluble and in blood are transported in complex with apolipoproteins, which render them soluble. These complexes, the lipoproteins arc classified into five groups, based on their size and lipid-to-protein ratio: chylomicrons, very low density lipoproteins (VLDL), intermediate density lipoproteins (IDL), low density lipoproteins (LDL), and high density lipoproteins (HDL). Chylomicrons are basically droplets of fat, and consist of TG to about 90%. Chylomicrons function as vehicles for the transport of dietary lipids from the ileum to adipose tissue and liver and are present in the general circulation for only a short period after a meal.

The four remaining classes of lipoprotein are produced in the liver. Whereas VLDL, IDL, and LDL are responsible for transporting lipids from the liver to the tissues, the fifth class, HDL is engaged in the reverse transport of superfluous lipids from peripheral tissues back to the liver for further hepatobiliary secretion. VLDL and IDL have short half-lives and deliver mainly TG to the tissues. LDL and HDL have longer half-lives and are the major participants in blood cholesterol homeostasis. On average LDL and HDL combined carry about 95% of the cholesterol present in blood, with LDL carrying about 70% and HDL about 25%.

There are five different types of proteins present in lipoproteins: apolipoprotein (Apo) A, B, C, D, and E, and each type may be further subdivided. The apolipoproteins are important for the formation, secretion, and transport of lipoproteins as well as the enzymatic activities working upon the lipoproteins in the peripheral tissues. Apolipoprotein B (ApoB) is the principal protein in VLDL, IDL, and LDL; in LDL, it is the only protein. HDL is devoid of apoB and its principal protein is apo-A1.

High concentrations of TG are associated with different pathophysiological disorders such as diabetes, cardiovascular disease, hyperlipidaemia, hyperglyceridaemia types I and IV, and nephritic syndromes. Low concentrations are found in hepatic infection and malnutrition.

From many epidemiological studies it is a well established fact that the CH associated with chylomicrons, VLDL, IDL, and LDL is a major risk factor for cardiovascular disease (CVD), with increasing concentrations correlating with increased risk of CVD. The CH associated with LDL particles is considered the main risk factor and is by far the largest of these components. CH associated with HDL on the other hand is inversely correlated with risk for cardiovascular disease. The lower the concentration of HDL, the higher the risk for cardiovascular disease. Therefore it is common practice to determine CH associated with LDL and/or HDL, typically along with total CH, to diagnose and predict cardiovascular disease, as well as in formulating the risk of CVD, potentially in combination with other factors.

Two methods are currently used routinely for quantification of CH. Both methods are enzymatic. In the first method is utilised an enzyme chain beginning with cholesterol esterase and cholesterol oxidase to generate a coloured or fluorescent signal by the generation of hydrogen peroxide. The other method substitutes cholesterol dehydrogenase in place of cholesterol oxidase and determines the amount of CH in the sample on the basis of the amount of the produced NADH or NADPH. These methods rely on the at least partial release of cholesterol from it lipoprotein carrier before the reaction can proceed effectively. Surfactants are generally used for this function and are well known in the art.

HDL associated CH may be determined by separating, either physically or by blocking, this class of lipoprotein from non-HDL lipoproteins. After making the non-HDL unavailable, HDL associated CH is measured using the enzymatic methods of total CH. This reaction cannot, however be run to its end point because the known methods of blocking are temporary and would become undone before the end-point was reached. The exception to this is where the non-HDL can be physically separated but this requires techniques such as centrifugation which are not available to point-or-care instruments.

Originally, and still much used, was precipitation of non-HDL by using one of the following:

(i) heparin/Mg2+ (Hainline A et al (1982) Manual of laboratory operations, lipid and lipoprotein analysis, 2nd ed. Bethesda, Md.: US department of Health and Human Services, 1982:151 pp), (ii) phosphotungstate-Mg2+ (Lopes-Virella M F et al (1977) Clin Chem 23:882-4), (iii) Polyethylene glycol (PEG) (Viikari J, (1976) Scan J Clin Lab Invest 35:265-8), and (iv) dextran sulfate-Mg2+ (Finley et al (1978) Clin Chem 24:931-3).

The precipitated non-HDL is then removed by centrifugation. The latter method is still recommended by the Cholesterol Reference Method Laboratory Network as reference method for measurement of HDL associated CH (Kimberly et al (1999) Clin Chem 45:1803-12).

Other methods used separation by electrophoresis (Conlin D et al (1979) 25:1965-9) or chromatography (Usui et al (2000) Clin Chem 46:63-72).

The above methods are effective, but require lengthy separation steps and a number of laboratory instruments. In order to eliminate the laborious sample pretreatment two different routes have been taken. Point-of-care instruments have been developed that integrate the separation and quantification of HDL into the test device, which may be cassettes or reagent-impregnated strips, such as the Cholestech HDL assay device and method (U.S. Pat. No. 5,213,965).

For the automatic clinical instruments, homogenous methods were developed which did not require a physical separation of non-HDL lipoproteins to measure the HDL associated CH fraction. The non-HDL particles were blocked by different methods and rendered inaccessible to the CH metabolizing enzymes. The most recent development has been highly specific surfactants that selectively dissolve HDL. IN such a situation, it is the reaction mixture for HDL which effectively "blocks" non-HDL by including only surfactants which leave non-HDL lipids in lipoprotein form and thus largely inaccessible to the action of the enzymes.

LDL associated cholesterol is commonly determined computationally using the Friedewald equation (Friedewald W T et al (1972) Clin Chem 18:499-501):

LDL=Total CH−(HDL+TG/2)

Although convenient and in most cases sufficiently accurate, this method suffers from well-known limitations, in particular the need for the patient to fast before being bled (fasting depletes blood of chylomicrons) and the requirement for TG levels to be below 4 g/L. Therefore the NIH sponsored National Cholesterol Education Program (NCEP) Adult Treatment Panel III (ATPIII) guidelines have recommended using direct measurement of LDL associated CH rather than computing it from total CH, HDL associated CH, and TG. However, recent reports question any clinical superiority of directly measured LDL levels over computed levels (Mora et al (2009) Clin Chem 55:888-94).

Originally, LDL associated CH was measured using ultracentrifugation (Havel R J et al, J Clin Invest 1955;34:1345-53). This is still the most used reference method, but evidently requires sample pre-treatment. Homogenous methods were later developed which did not require a physical separation of non-LDL lipoproteins to measure the LDL CH fraction (U.S. Pat. Nos. 5,888,827, 5,925,534).

VLDL associated CH was originally measured using ultracentrifugation. This remains a preferred reference method, but during recent years homogenous methods for determining VLDL associated CH have been developed. These include methods from U.S. Pat. Nos. 6,986,998and 7,208,287.

CH associated with IDL (also called "VLDL remnants" or "remnant-like particles") is commonly determined using ultracentrifugation, high performance liquid chromatography or electrophoresis. Two homogenous methods were recently developed (U.S. Pat. No. 7,272,047 and US 2007/0161068) that use specific surfactants to further the selective enzymatic decomposition of IDL associated cholesterol.

In recent years several reports have suggested that measurement of nonHDL may prevent more cardiac events than measurement of LDL (van Deventer et al Clin Chem (2011) 57:490-501; Sniderman et al (2011) Circ Cardiovasc Outcomes 4:337-45). In particualt nonHDL may be superior at elevated TG levels (Sniderman et al (2010) J Clin Lipidol 4:152-5). NonHDL is currently not directly measured by any known prior assay method but computed as the difference between total CH and cholesterol associated with HDL (nonHDL=Total CH−HDL)". The present invention, however allows for direct or indirect (calculated) measurement of non-HDL components. In one aspect of the present invention, at least one of the analytes is bound to the group of non-HDL lipoproteins. In particular, non-HDL cholesterol is a highly preferred analyte. Non-HDL cholesterol may be measured, for example, in a lipid panel assay along with total TG and total CH.

For screening purposes a direct assay for nonHDL will have the advantage of reducing assay time and cost compared to running two assays, Total CH and HDL and computing the nonHDL as the difference (Example 10). Thus, in a further aspect, of the present invention, one analyte will be bound to the non-HD lipoproteins (such as non-HDL cholesterol) and will be measured directly (i.e. not by taking the difference between two other measurements). This analyte may be measured with or without any other analytes. Furthermore, the advantages of measuring non-HDL (eg non-HDL CH) directly extend to assays which used end-point estimation (i.e. the calculation of a fictive end point as described herein) and also assays that use conventional techniques. Thus in a further aspect the invention provides an assay for the direct measurement of a lipid component bound to non-HD lipoprotein, such as non-HD cholesterol. A corresponding method for assigning a risk of or propensity to CVD is provided by comparing such a value to an appropriate threshold, such as a threshold derived from populations of healthy individuals and/or individuals suffering from a high risk or propensity to CVD.

TG is determined routinely in a four step enzymatic reaction, in which lipoprotein lipase hydrolyzes TG to unesterified glycerol and free fatty acids. The glycerol is then phosphorylated (glycerokinase) and oxidized (glycerol-3-phosphate oxidase) to di-hydroxy-acetone-phosphate and hydrogen peroxide, which is used to generate a coloured, fluorescent or chemiluminescent signal.

As with the measurement of CH of different lipoprotein classes, measurement of TG of specific lipoprotein classes may be performed by several methods that exploit different chemical and physical characteristics of the different lipoprotein classes.

As discussed above the measurement of a lipid component of a specific lipoprotein class, e.g. cholesterol in HDL, constitutes a particular problem for point-of-care assays. Current methods depend on temporarily blocking the particular lipid component present in lipoproteins other than the specific lipoprotein class and then measuring the particular lipid component associated with the specific lipoprotein class. Such methods rely on blocking the unwanted lipoproteins with synthetic polymers and polyanions (U.S. Pat. Nos. 5,577,3304, 6,811,994) or antibodies (U.S. Pat. Nos. 4,828, 986, 6,162,607) or cyclodextrin combined with polyethylene glycol modified enzymes (U.S. Pat. No. 5,691,159), or use specific surfactants (U.S. Pat. Nos. 7,208,287, 7,272,047).

Because the blockage is temporary a true end-point for these reactions is not possible to measure, the only true end-point is the end-point of the particular lipid component present in all four classes of lipoprotein. The particular lipid component of the specific lipoprotein is therefore measured either at a fixed time point, chosen so that the particular lipid component present in lipoproteins other than the specific lipoprotein does not interfere substantially (usually 5 minutes), or kinetically during the first minutes of the reaction. In both cases is required either fully stable reagents, i.e. dry reagents, or inclusion of calibrators, to compensate for long-term reagent decay.

A different approach is to eliminate selectively the particular lipid component associated with lipoproteins other than the specific lipoprotein class being analyzed, in an enzymatic reaction not giving detectable product. The particular lipid component of the specific protein class is then converted into a detectable product. Several such methods have been described making use of surfactants that react selectively with specific lipoprotein classes (EP 1164376, U.S. Pat. Nos. 5,925,534, 6,194,164, 6,818,414, 6,893,832).

However, in order to accomplish complete elimination the reaction must be allowed to reach end-point, and that takes time. The time required for this would be too long time for point-of-care assays and in particular for point-of-care assays measuring a plurality of analytes, (known as "panel" assays). In addition, these approaches have problems with inaccuracies caused by an incomplete elimination of the particular lipid constituent in lipoproteins other than the specific lipoprotein being analyzed or by non-specific elimination of the particular lipid constituent in the specific lipoprotein. In practise, then, these types of assays also require fixed-point measurement and thus rely on either fully stable reagents, i.e. dry reagents, or inclusion of calibrators, to compensate for long-term reagent decay.

In view of the above, there is evidently a need for improved point-of-care assays for measuring one or a plurality of plasma components (such as lipid components) and in particular for assays including lipid components of specific lipoprotein classes. It would be advantageous if such assays allowed for liquid reagents, did not require calibrators and/or had short total assay times.

The inventors now have established that it is possible to construct an assay method, suitable for the point-of-care apparatus that uses blood-cell containing samples (such as whole blood), uses liquid reagents, has a short total assay time and does not require calibrators.

The inventors surprisingly have found that it possible to determine an end-point for an enzymatic reaction where that end point is theoretically unreachable and/or in practice unmeasurable. This allows many of the advantages of end-point analysis to be applied in situations where end-points have previously not been considered. For example, in a sequence involving several enzymes, product will be consumed and thus the end point cannot be reached. Also, in those cases where an end-point cannot be directly measured, such as in consecutive enzyme reactions where the next step starts before the preceding reaction has reached an end-point, or in parallel enzyme reactions where there is a sufficient difference in the early progress of the reactions.

In situations where the end point cannot be or is not measured, it may be computed using a suitable algorithm rather than directly measured, with accuracy and CV similar to those achieved with direct measurement. What is needed is for the reaction to be monitored for a sufficient length of time and then using a suitable algorithm to accurately predict the end-point. Suitable algorithms and equations have been regularly used in the art for curve-fitting purposes and are thus well-known, but have not previously been applied in this way to predict an end point that cannot be measured. Typically, the reaction should be monitored until at least 50% of the target analyte has been converted, although this may constitute only a minor fraction of the progress curve. Monitoring the reaction until at least 40%, preferably at least 50% and optionally at least 60% of the target analyte has been consumed is appropriate in various embodiments.

In one embodiment, it is preferable that the measurement interval is chosen such that any parallel reactions (such as unblocking and reacting of any blocked components) are not significant.

In an alternative embodiment, parallel reactions such as unblocking and reacting of any blocked components may take place to a measureable extent but the influence of such parallel reactions may be to a certain extent corrected for by post-measurement analysis where more than one analyte from the sample is measured. For instance when a plurality of lipid analytes are measured, such as in a lipid panel assay, the interference of nonHDL on HDL measurements (such as by partial unblocking and reaction of the non-HDL component) may be partly corrected for in an iterative process involving the readings for HDL and total cholesterol, according to Total cholesterol=HDL+nonHDL, and a predetermined standard curve for the effect of non-HDL on the HDL assay (Example 6).

The inventors also have found that using end-point estimation with reactions that produce measurable end-points may afford substantial advantages to point-of-care assays using liquid reagents. Measurement of end-points must take into consideration the effect on assay time of loss of reagent activity with storage time, using estimated end-points avoids this and consequently allows for shorter measurement times to be used.

BRIEF SUMMARY OF THE INVENTION

In a first aspect, the present invention thus provides an enzymatic method for measuring the concentrations of at least one analyte in the plasma portion of a blood-cell containing sample, wherein the sample contains a first component and a second component, where said second component interferes with the measurement of said first component if said second component is present and unblocked, said method comprising the steps of i) contacting said blood cell containing sample with a reagent mixture that dilutes the sample;

ii) substantially removing blood cells to provide a substantially cell free sample;

iii) contacting said sample with at least one reagent which serves to temporarily and/or competitively prevent reaction of said second component, whereby to generate a blocked second component;

iv) contacting said sample with at least one reagent mixture comprising at least one converting enzyme for at least one constituent of each analyte of said at least one analyte, whereby to cause the selective reaction of the or each analyte to directly or indirectly generate detectable reaction products, wherein the, or one of, said analytes is said first component;

v) monitoring said detectable reaction product or products;

vi) relating an amount of said detectable product or products and/or a rate of formation of said detectable product or products to the concentration of the or each of said at least one analyte in said blood sample, wherein the concentration of at least said first component is related to a corresponding detectable reaction product by means of estimating an umeasurable (fictive) endpoint;

wherein step iii) may be carried out at any stage up to and including step iv) but before steps v) to vi) and wherein the reagent of step iii) may be applied to the sample separately or may be included in the reagent mixture of steps i) or iv).

In a preferred aspect, the method will be for the concomitant (e.g. simultaneous) measurement of a plurality of analytes, such as two, three or more analytes, in said cell-containing sample.

In all aspects of the invention, where detection of a detectable "product" is indicated, this will evidently also allow for the detection of a detectable reactant or starting material, where context allows. The only change that will need to be made in most cases is that the reactant or starting material will be consumed and thus concentration will decrease. Since product and starting material are typically related by known stochiometry, decrease in reactant is thus an indirect method for detecting product. All appropriate product detection may thus be carried out by means of observing consumption of one or more reactants.

In a further aspect, the present invention additionally provides A kit for use in determining the concentration of at least three different analytes in the plasma portion of a blood-cell containing sample, wherein the sample contains a first component and a second component, where said second component interferes with the measurement of said first component if said second component is present and unblocked, said kit comprising;

a) a first reagent mixture formulated to dilute said sample;
b) a cell separation unit;
c) a second reagent which serves to temporarily and/or competitively prevent reaction of (block) said second component, whereby to generate a blocked second component;
d) at least three further reagent mixtures formulated to cause the selective conversion of said at least three different analytes, whereby to generate detectable indirect products corresponding to each analyte.

DETAILED DESCRIPTION OF THE INVENTION

The present invention provides for an assay method in which the concentration of at least one analyte in a blood-cell containing sample is measured.

As used herein, the term "analyte" is used to indicate a component or group of components whose measurement is desired. Analytes may thus be a single component, such as HDL cholesterol, or may be a set of components. Typically such a set will have a common feature, such as the set of all cholesterol containing lipoproteins.

Among the most preferred analytes for use in the present invention are lipid components, which is to say the total amount of a particular type of lipid (e.g. TG or CH) in the plasma portion of the sample or that part of a particular type of lipid present as a particular lipoprotein (e.g. HDL CH) or a particular set of lipoproteins (e.g. non-HDL CH).

The use of end-point estimation is useful in assays for a single component, where the end-point of the conversion of a particular constituent of that component (e.g. conversion of the lipid constituent of HDL) will be estimated by the methods indicated herein. The technique is, however, also highly valuable in parallel assays for multiple analytes (often termed "panel assays"). This applies particularly at the point-of-care. In such cases, two, three, four, five or more analytes may be measured in the assay. Furthermore, the instrument may be able to calculate the level of other analytes from the measured data and thus may be able to report on more components than are measured directly (see the discussions herein for example). In the panel assay embodiment of the invention it is preferable that at least three analytes are measured.

Where at least two (e.g. at least three) analytes are measured, end-point estimation methods will be used for analysis of one or more of such analytes. Where at least one analyte is a first component which cannot conveniently/reliably be measured without blocking of another component then this first component will be analysed by estimation of an immeasurable (fictive) endpoint. In combination with this method, however, other components that could be measured by end-point methods may also be measured by end-point estimation in order to reduce the time required for the total assay. Thus in one embodiment all analytes are measured by end-point estimation methods with at least one analyte being measured by estimation of an unmeasurable (fictive) endpoint.

As indicated above, preferred analytes are lipid components of the blood sample. Typical analytes will thus be cholesterol, triglycerides or phospholipid, in total and/or associated with a specific lipoprotein from the group consisting of VLDL, IDL, LDL and HDL. Cholesterol, triglycerides and/or phospholipid associated with groups of lipoproteins (e.g. non-HDL CH) may also be measured and form further preferred analytes.

The "first component" referred to herein will typically be a particular lipid associated with a particular lipoprotein (or group of lipoproteins) such as HDL_CH or non-HDL-CH. Thus, typically said first component is one analyte having a lipid constituent selected from cholesterol, triglycerides or phospholipid associated with at least one lipoprotein constituent selected from VLDL, IDL, LDL and HDL, such as cholesterol associated with HDL.

The interference caused between the "second component" and the measurement of the "first component" as indicated herein will generally be due to the need to distinguish the reaction of the lipid constituent of the first component from that of the second. Typically, therefore, the first and second components will comprise the same lipid constituent(s). In a typical example, it may be desired to measure HDL-CH (first component and analyte) in the presence of non-HDL-CH (second component). This cannot easily be done without "blocking" of the second component because the lipid constituents are both CH and thus if both are allowed to react then it is not possible to distinguish between them. In such situations the second component is "blocked" so that only or primarily the first component is available for reaction.

There are many methods by which components (especially the "second component" as discussed herein) may be "blocked". Many of these methods are discussed herein and others are known to the skilled worker. If such a blocking is or can be made permanent (e.g. by some covalent attachment of a blocking moiety) then end-point estimation is not necessary (although it may still be an advantage in order to speed the assay method). However, techniques currently know and/or widely used are "temporary" blocking methods, which is to say the second component is rendered fully or largely uncreative but re-gains this reactivity either independently or in the presence of the enzymatic conversion reagents and/or surfactants employed in step iv) of the processes described herein. As used herein, a reagent that serves to "temporarily" prevent reaction of a component will prevent significant reaction of that component under appropriate conditions (e.g. the conditions of step iv)) for at least 60 seconds, preferably at least 240 seconds and most preferably at least 360 seconds. By significant reaction is indicated reaction of more than 10%, preferably more than 5% and most preferably reaction of more than 3% of any constituent (e.g. the lipid part) of that component.

Correspondingly, a "blocked" component will not undergo reaction of its lipid constituent to an extent of more than 10%, preferably 5%, more preferably 3% over a period of at least 60 seconds, preferably at least 240 seconds, more preferably at least 360 seconds when subjected to reactive conditions, such as the conditions of step iv) as described in any embodiment herein.

In preferred embodiments, the conditions of steps i), ii) and/or iii) are chosen such that the cells of the blood sample remain intact, or substantially intact (e.g. less than 10% of the cells, preferably less than 5%, and most preferably less than 3% (e.g. 0.1 to 3%) of the cells suffer lysis during steps i)-iii). Factors including ionic strength and surfactant type/concentration are particularly important in this respect.

Optionally, reaction accelerators such as disclosed in U.S. Pat. No. 6,818,414 may be included in the reagent solution, especially at step iv) to increase reaction rate and thus decrease assay time.

In the present invention, the method and other aspects relate to the measurement of at least one analyte. Such analytes will typically be lipid analytes and each independently may the total amount of a certain lipid component such as triglyceride, cholesterol, etc or may be a lipid component associated with a specific lipoprotein or a group of specific lipoproteins. Non-exhaustive examples of these include all combinations of lipid components cholesterol, triglycerides or phospholipid with any of lipoproteins VLDL, IDL, LDL and HDL, as well as the corresponding parts of each total lipid component not associated with such lipoproteing. Thus, for example, analytes include HDL cholesterol and non-HDL cholesterol, the latter being that part of the total cholesterol not bound to the HDL lipoprotein. Particularly preferred analytes include total TG, total CH, nonHDL, LDL, small dense LDL and HDL cholesterol.

In order to measure the parts of certain lipid components associated with specific lipoproteins, it is necessary to "block" or render uncreative either that component or all other lipoproteins having the same lipid component. This allows measurement of one component in the presence of another which would normally interfere.

Although this blocking is in itself known and many examples are described herein below, the known methods for achieving this do not result in a permanent blockage or do not hold the lipid component permanently. Rather, after a certain period and/or if the concentration of the lipid component elsewhere in the sample falls too low then the blockage will begin to fail and the lipid component will become reactive. Thus, in such situations, a reaction consuming the same lipid constituent as is constituted in a blocked component cannot be run to its endpoint because the blockage would become ineffective before that point was reached. Such endpoints are described herein as "unreachable", "unmeasureable" or "fictive" to reflect the fact that they can never in fact be reached.

In view of the above, has been assumed in the art that endpoint type assays cannot be used with blocked lipid components of this type because the endpoint is "unmeasureable". This has resulted in the need to use calibration or more commonly dried reagents in such assays with all of the disadvantages associated with those (as known in the art and as described herein).

However, the present inventors have now established that end-point estimation techniques can be effectively used even on such unmeasurable endpoints and so that unreachable or unmeasureable ("fictive") endpoint can still be calculated even if it can never be reached in practice.

With regard to the selective reaction of specific class of lipid or specific class of lipoprotein, and the conversion of the lipid constituent of a lipoprotein to detectable secondary analyte, there are a number of methods which are well known in the art and any of these are suitable for use in the present invention. All of the homogeneous methods described above are suitable and included within the scope of the invention. Further details arc supplied below and in the referenced citations.

Two methods arc currently used routinely for quantification of CH. Both methods are enzymatic and suitable for use in the method of the present invention. In the first method, cholesterol esterase converts cholesterol esters into CH. Cholesterol oxidase then converts CH to choleste-4-ene-3-one and hydrogen peroxide. Finally hydrogen peroxidase uses the hydrogen peroxide formed to convert 4-aminoantipyrin in the presence of phenol to generate a coloured quinoneimine compound. The quinoneimine is monitored by photometry at 500-600 nm wavelength. Other well known colour producing substrates (e.g. TMB which product is blue and monitored at 650 nm) or fluorescent or chemiluminescent substrates may be substituted for the 4-aminoantipyrin/phenol.

The other method substitutes cholesterol dehydrogenase for cholesterol oxidase and determines the amount of CH in the sample on the basis of the amount of the produced NADH or NADPH.

With regard to the detection of TG, this is determined routinely in a four step enzymatic reaction, in which lipoprotein lipase hydrolyzes TG to unesterified glycerol and free fatty acids. The glycerol is then phosphorylated by glycerokinase and oxidized by glycerol-3-phosphate oxidase to di-hydroxy-acetone-phosphate and hydrogen peroxide. In a final colour forming step hydrogen peroxidase uses the hydrogen peroxide formed to convert 4-aminoantipyrin in the presence of phenol into a coloured quinoneimine. The quinoneimine is monitored spectrophotometrically at 500 nm wavelength. By selecting the appropriate substrates and phenols the formed coloured products may be monitored at wavelengths from 450 to 850 nm. Likewise fluorescent or chemiluminescent substrates may be substituted for the 4-aminoantipyrin. Evidently, the final steps in both peroxide-based methods are equivalent and interchangable.

Thus, the enzyme reactions converting the specific plasma lipid component into a detectable chemical product preferably may be performed using the above described enzyme systems.

For CH:
(i) cholesterol esterase+cholesterol oxidase+peroxidase, or
(ii) cholesterol esterase+cholesterol dehydrogenase.

For TG:
(iii) lipase+glycerol kinase+glycerol-3-phosphate oxidase+peroxidase.

As enzymes, commercially available enzymes derived from animals, micro-organisms or plants may be used. Enzymes from specific sources may display selectivity for certain lipoprotein classes, such as lipoprotein lipase and cholesterol esterase from Chromobacterium viscosum or Pseudomonas which react preferentially with the lipoprotein class VLDL. Such enzymes may be used to assay for a specific component, either in isolation or in combination with the other selection methods described herein. The enzymes may be chemically modified so as to change their specificity and stability, e.g conjugation of cholesterol oxidase and cholesterol esterase with PEG in order to make the enzymes less reactive with LDL associated CH (U.S. Pat. No. 5,807,696). Enzymes are typically used at concentrations from 100-100,000 U/L.

Measurement of lipid components of specific lipoprotein classes may be performed by several methods that exploit different chemical and physical characteristics of the different lipoprotein classes. In general, these methods rely on the specificity of the enzyme, and/or allow the reaction of the desired component after separating, converting or rendering inactive those other components which might interfere.

Non-ionic, anionic, cationic, and zwitterionic surfactants may be included in order to increase the selectivity of the enzymatic reactions or to increase the rate of reactions. Any suitable surfactant may be used that allows maintaining the intact status of the cells during the course of the reactions. One property of non-ionic surfactants of particular importance for the status of cells, is the hydrophil-lipophil balance (HLB). Surfactants with HLB values below 10 and above 13 are in particular suitable for use in the presence of intact cells. However, surfactants with HLB values between 10 and 13 may also be compatible with intact cells depending on the concentrations used, and depending on the construction and formulation of the assay, such as reaction times and temperatures used, ion strength, pH and types of salts used in the assay mixture, and the presence of stabilizing substances such as serum albumin. Examples of suitable surfactants are polyoxyethylene alkyl ethers (Brij 35 and 78), polyoxyethylene alkyl aryl ethers (Triton X45 and X305, Igepal 210 and 272), polyoxyethylene sorbitan monolaurate monolaurate (Tween 80), polyoxyethylene-cooxypropylene block copolymer (Pluronic F68 and L64), telomere B monoether with polyethylene glycol (Zonyl FSN 100), ethylenediamine alkoxalate block copolymer (Tetronic 1307), 2,4,7,9-tetramethyl-5-decyne-4,7-diol ethoxylate (Surfonyl 465 and 485), polydimethylsiloxane methylethoxylate (Silwet L7600), polyethoxylated oleyl alcohol (Rhodasurf ON-870), polyethoxylated castor oil (Cremophor EL), p-isononylphenoxy-poly(glycidol) (Surfactant 10G), and a polyether sulfonate (Triton X200). Surfactants are used for this purpose typically at concentrations of 0.001-10%, preferably 0.01 to 1%.

The following methods are among those suitable for selectively reacting the particular lipoprotein components as described. In all cases, the referenced published material is incorporated herein by reference.

In homogenous methods to measure the HDL associated CH fraction, the non-HDL particles have been blocked from reaction by different methods and rendered inaccessible to the CH metabolizing enzymes. The most recent development has been specific surfactants that selectively dissolve HDL. These include:

(i) In the PEG/cyclodextrin method (U.S. Pat. No. 5,691,159) sulfated alpha-cyclodextrins in the presence of $Mg^{2+}$ forms soluble complexes with non-HDL which thereby become refractory to breakdown by PEG modified enzymes.

(ii) The polyanion method (U.S. Pat. No. 5,773,304) uses a synthetic polymer together with a polyanion, or a surfactant (U.S. Pat. No. 7,851,174) to block non-HDL and make them refractory to solubilization with specific detergents and enzymatic measurement.

(iii) The immunologic method (U.S. Pat. No. 6,162,607) exploits the presence of apolipoprotein B in all non-HDL and its absence in HDL. Antibodies to apoB block non-HDL for reaction with the cholesterol enzymes.

(iv) In the clearance method (U.S. Pat. No. 6,479,249) non-HDL is first consumed in a reaction not generating colour. A specific detergent is then added allowing the enzymes to react with HDL in a reaction generating colour.

(v) The accelerator/detergent method (U.S. Pat. No. 6,818,414) degrades unesterified cholesterol of non-HDL using an accelerator to speed up the reaction, and removes the formed H2O2 in a process not generating colour. In a second step HDL cholesterol is degraded using an HDL-specific detergent in a colour forming process.

Any of these methods, either individually or in combination may be applied to the measurement of HDL associated CH in the method of the present invention. LDL associated CH has been measured by homogenous methods which did not require a physical separation of non-LDL lipoproteins to measure the LDL CH fraction. Such methods include:

(i) U.S. Pat. No. 5,888,827 describes a method whereby non-LDL is masked by surfactants and cyclodextrins in the presence of $Mg^{2+}$ and becomes refractory to breakdown by PEG modified enzymes.

(ii) U.S. Pat. No. 5,925,534 describes a method using polyanions and surfactants to protect LDL in a sample and allow non-LDL to be enzymatically eliminated whereupon addition of a deprotecting reagent allows the enzymatic determination of LDL associated CH.

(iii) U.S. Pat. Nos. 6,057,118 and 6,194,164 describe two different methods utilizing specific surfactants to selectively eliminate non-LDL associated CH in an enzymatic reaction before determining LDL associated CH.

During recent years homogenous methods for determining VLDL associated CH have been developed. These include:

(i) U.S. Pat. No. 6,986,998 describes a method using albumin and calixarene to block HDL and LDL, respectively, allowing the selective decomposition of VLDL in an enzymatic reaction using VLDL selective enzymes from Chromobacterium viscosum.

(ii) U.S. Pat. No. 7,208,287 describes a method using specific surfactants to selectively decompose VLDL in an enzymatic reaction.

Cholesterol associated with IDL (also called "VLDL remnants" or "remnant-like particles") is commonly determined using ultracentrifugation, high performance liquid chromatography or electrophoresis. Two homogenous methods were recently developed (U.S. Pat. No. 7,272,047 and US 2007/0161068) that use specific surfactants to further the selective enzymatic decomposition of IDL associated cholesterol. Any of these methods, either individually or in combination may be applied to the measurement of LDL associated CH in the method of the present invention.

Measurement of TG of specific lipoprotein classes may be performed by methods that exploit different chemical and physical characteristics of the different lipoprotein classes. These methods are thus analogous to those described above for cholesterol, but utilising enzymatic detection of TG, such as by those methods described herein above. Such methods include:

(i) U.S. Pat. No. 6,811,994 describes using selective surfactants and polyethylene glycol modified enzymes to block lipoproteins other than the particular lipoprotein.

(ii) WO2004/087945 and US2009/0226944 describe using selective surfactants to remove TG from nonLDL in a reaction not producing detectable products then converting TG associated with LDL into detectable products.

(iii) WO2000/06112 describes using selective surfactants to remove TG from lipoprotein other than VLDL and/or IDL in a reaction not producing detectable products then converting TG associated with VLDL and/or IDL into detectable products.

Any of these methods, either individually or in combination may be applied to the measurement of TG associated with specific lipoproteins in the method of the present invention.

The detection method used in the assay methods of the present invention is typically photometric, and the indirect product is generally chosen such that it is detectable photometrically (e.g. by its absorbance, fluorescence or chemiluminescence at one or more pre-identified wavelengths).

A highly preferred method for signal generation is via hydrogen peroxide, which serves as a substrate for the enzymatic oxidation of a colour-producing substance. The oxidizable color producing reagent or reagents that react with formed hydrogen peroxide to produce the detectable chemical product may be any molecule known in the art, the oxidized product of which can be measured by ultraviolet, visual, or infra-red spectroscopy, or by fluorescence or luminescence.

Examples of suitable chromogenic reagents are Trinder reagents, which in the presence of $H_2O_2$ react with a coupler to form colored products. Preferred examples of couplers are 4-aminoantipyrin (4AA), 3-methyl-2-benzolinone hydrazone (MBTH), N-methyl-N-phenyl-4-aminoaniline (NCP-04), N-methyl-N-(3-methylphenyl)-4-aminoaniline (NCP-05), N-methyl-N-(3-methoxyphenyl)-4-aminoaniline (NCP-06), N-methyl-N-(3-methoxyphenyl)-3-methoxy-4-aminoaniline (NCP-07). Preferred examples of Trinder reagents are those forming products that can be colorimetrically determined at wavelengths at or above 600 nm: N-Ethyl-N-(2-hydroxy-3-sulfopropyl)-3,5-dimethyloxyaniline (DAOS), N-Ethyl-N-(2-hydroxy-3-sulfopropyl)-3,5-dimethoxy-4-fluoroaniline (FDAOS), N-(2-hydroxy-3-sulfopropyl)-3,5-dimethoxyaniline (HDAOS), N,N-bis(4-sulfobutyl)-3,5-dimethylaniline (MADB), N-ethyl-N-(2-hydroxy-3-sulfoprpyl)-3,5-dimethylaniline (MAOS). Preferred examples that are not Trinder reagents are: 3,3',5,5'-Tetramethylbenzidine (TMB), N-(3-sulfopropyl)-3,3',5,5'-tetramethylbenzidine (TMBZ-PS), N,N-bis(2-hydroxy-3-sulfopropyl)tolidine (SAT Blue), N-(carboxymethyl-aminocarbonyl)-4,4-bis(dimethylamino)-biphenyl amine (DA64), 10-(carboxymethylaminocarbonyl)-3,7-bis(dimethylamino)phenotiazine (DA67). The concentration of the chromogen is preferably 0.01-10 g/L, and is limited by solubility.

Examples of suitable fluorescent substrates are dihydrocalceins, dihydroethidium, dihydrofluoresceins, dihydrophenoxazine (Amplex red;10-acetyl-3,7-dihydroxyphenoxazine), and dihydrorhodamines.

Examples of suitable chemiluminescent substrates are luminol (3-aminotriphenylene complexes), Lumigen PS-2 and Lumigen PS-atto.

Non-ionic, anionic, cationic, and zwitterionic surfactants may be used for the purpose of cell lysis prior to measurement of colored indirect analyte. Any suitable surfactant may be used that does not affect the measurement, typically at concentrations between 0.01-10%, but preferably between 0.1-2%.

Examples of suitable surfactants are the anionic surfactants amine aklylbenzene sulfonate (Ninate 411), sodium dioctylsulfosuccinate (Aerosol OT), sodium N-oleyl-N-methyltaurate (Geropon T-77), sodium olefin sulfonate (Bioterge AS-40), sodium polyoxyethylene lauryl sulphate (Standapol ES-1), and the non-ionic surfactants polyoxyethylene alkyl aryl ether (Triton X100 and X114) and polyoxyethylene lauryl alcohol (Chemal LA-9).

Where cell lysis has occurred, there will evidently be a corresponding release of haemoglobin and other cell products into the reaction medium. In order to gain maximum advantage from the lysis and reduce the background signal as far as possible, it is thus preferred in such cases to select a product (secondary analyte) for which detection is not inhibited by these released products. Secondary analytes detectable at wavelengths above 450 nm, preferably above 500 nm and most preferably 600 nm or higher (e.g. 500 to 1400 nm or 600 to 1200 nm) are thus preferred where cell lysis is used.

Physical separation of blood cells in the sample may be performed by any suitable method including flow past a specific binder for the whole cells, but will most commonly be by filtration. It is notable that filtration to remove cells following reaction step (i) has considerable advantages over filtration of the original blood sample. In particular, the reaction step can be carried out with a small volume of blood sample from a finger-stick. After one or more reagents have been added, the volume of the reaction mixture is much greater and separation of the cells can be conducted without the dead-volume being significant. The cells are also more dilute, whereby the cells upon filtration will spread more evenly over the filter surface and the filtration becomes more effective.

Filtration as described herein is thus a preferred technique for use in setp ii) of the methods of the present invention and corresponding filters etc are suitable for supply with the kits of the invention. Some preferred embodiments of such filtration are provided below, any of which may be applied individually or in any combination to the methods and kits of the invention.

In filtering, the sample is passed through a porous interface (filter, membrane or sieve) of small pore size, in which the cells are trapped. The porous interface may be solid (e.g. sintered glass) or fibrous (e.g. made of cellulose or glass), and the flow may be transversely through or laterally. The sample may be passed through the filter by gravity, centrifugation, capillary forces, pressure or suction. The filtering material may additionally contain reagents (e.g. lectins, antibodies) that capture the blood cells. Other methods use electrostatic attractions.

Suitable materials for transverse filtering are given in Table 2. Suitable materials for lateral flow filtering are Hemasep® L (Pall Corp) and LF1 and MF1 (Whatman).

TABLE 2

Filtration recovery of lipids and colored product

| Filter type | TG (%) | CH (%) | HDL (%) |
|---|---|---|---|
| No filtration | 100 | 100 | 100 |
| PAD 901 | 99 | 95 | 97 |
| PAD Whatman | 98 | 92 | 94 |
| QA Pall | 102 | 96 | 97 |
| Whatman grade CF/CM30 | 103 | 99 | 97 |
| Gelman ITLC SG | 103 | 96 | 99 |
| Gelman A/E | 103 | 98 | 98 |
| Munktell filter paper | 101 | 97 | 98 |

Mathematical treatment of enzyme progress curves based on absorbance readings in order to calculate enzyme activities is well-known. Such mathematical procedures, algorithms are based on the integrated Michelis-Menten equation (London J W (1977) Analytical Chemistry 48:1716-9). However, the purpose of such algorithms is to determine enzyme activities by extrapolating the rate to zero time, they are not applicable to the determination of product end-points.

Recently, one group reported that using a combination of fixed time and kinetic measurements allowed the reading of the progress curve to be terminated when it had reached 90-95% of the predicted end-point, rather than following it to the end. This allowed for a substantially shortened assay time (Kvam (2009) Point of Care 8:16-20).

What the inventors have now surprisingly found is that in reactions without a measureable end-point it is still possible to estimate a fictive end-point which is a direct representative of the true, non-measurable end-point (FIG. 1). This will allow for circumventing the problems with fix-point measurements and their requirements for calibrators and/or dry reagents. What is needed is a suitable algorithm and at least 50% of the progress curve (e.g. at least 60% or at least 70%).

The algorithm used to predict the unmeasurable or fictive end-point in the various aspects of the present invention can be any mathematical equation that adequately describes the reaction progress, and might be used to describe the curve formed when such progress is plotted. Many such equations will be known to those of skill in the art. Usually the algorithm will be one based upon a first order rate equation (e.g. $Y=Y_0*e^{(-kX)}$) or a logistic function (e.g. $Y=1/(1+e^{(-X)})$) (Table 3). Which algorithm will be most preferable for a particular situation will depend on many factors such as how the measurement is performed (transmission or absorbance), reaction conditions (e.g. reaction temperature), as well as measurement interval and other factors. It will, however, be a routine matter to fit the curves from each suitable equation to the experimental data and thereby determine the closest fit in each case. Different instrument platforms may thus favour different curve fitting algorithms but a suitable algorithm in each case will be rapidly established. In many cases more than one algorithm will give acceptable results.

TABLE 3

Some Examples of reaction-curve fitting algorithms

| Type | Equation |
| --- | --- |
| 1st order (Exponential association/dissociation) | $Y = Y_{max} + (Y_0 - Y_{max})*e^{(-kX)}$ |
| 1st order-2 | $Y = Y_{max} - Y_{max}*e^{(-k(X - X_0))}$ |
| 1st order-3 | $Y = Y_{max} + (Y_0 - Y_{max})*e^{(-kX)} + X*C$ |
| Logistic-1 (Sigmoidal) | $Y = Y_0 + (Y_{max} - Y_0)/(1 + 10^{(logX_{50} - logX)*B})$ |
| Logistic-2 (4 parameter logistic) | $Y = Y_{max} + (Y_0 - Y_{max})/(1 + (X/X_{50})^B)$ |
| Logistic-3 | $Y = Y_0 + (Y_{max} - Y_0)/(1 + (X/X_{50})^B)$ |
| Logistic-4 | $Y = Y_{max} + (Y_0 - Y_{max})/(1 + (X/X_{50})^B) + X*C$ |

$Y_0$, Y at X = 0;
$Y_{max}$, Y at X = infinite;
k, rate constant;
$X_{50}$, X at half maximal Y;
B, slope factor, steepness of slope;
C, slope factor of parallel reaction..

When estimating an unmeasurable end-point, the measurement interval should preferably be chosen such that a minimum of parallel reactions are occurring. However, it is not a strict requirement that parallel reactions cannot be present. The influence of such parallel reactions may be corrected for in a post-measurement analysis. This is particuarly true where at least two analytes are measured in the sample and a known (absolute or approximate) relationship is present between at least two of said analytes.

For instance, in the HDL assay the estimated unmeasurable end-point may be influenced by a concomitant conversion of nonHDL, also when nonHDL has been rendered temporarily unreactive by blocking reagents depending on different factors such as (i) the measurement interval, (ii) reaction temperature, (iii) HDL/nonHDL ratio. In a lipid-panel assay this may be corrected for in an iterative process involving HDL the simultaneously measured total cholesterol and a calibration curve for nonHDL, determined in advance and placed in the information (e.g. barcode) supplied for the reagent, in the same way as done with the HDL calibration curve. An example of how a post-analysis correction may be carried out is described in Example 6.

It would also be possible to take into account parallel reactions occurring in the algorithm used to estimate the unmeasurable end-point. For instance the reaction conditions may be formulated such that parallel reactions are essentially linear during the measurement interval, and can be represented in the algorithm by a linear term (Table 3).

One of the considerable advantages of the present assay method is the resultant decrease in the assay time. It is thus preferable that the time from adding the reagent in step i) to end of the the monitoring of detectable reaction products in step v) is no more than 10 minutes, more preferably no greater than 8 minutes, and most preferably in the range 5 to 7 minutes.

It is a further advantage of the present invention that it may be carried out on a minimal volume of blood. It is preferred, therefore that the volume of whole blood sample in step i) of the assay method is no greater than 40 µL, more preferably no greater than 20 µL and most preferably in the range of 10 to 15 µL.

The present inventors have additionally established that further reaction time may be saved by the early contact of the sample with the "blocking reagent" (the reagent which serves to temporarily prevent reaction of said second component). This blocking reagent (many of which are described herein) typically takes some time (several minutes) to react with the second component. Thus, a typical point-of-care assay in which this blocking reagent was added at or around step iv) of the method would then be delayed by several minutes to allow reaction of this blocking reagent.

The present inventors have now established that it is possible to add a suitable blocking reagent to the cell-containing blood sample (e.g. whole blood sample) without significantly lysing the cells such that this reagent can be reacting with the second component of the sample during the cell separation steps(s). Evidently, this reduces the need to wait for the blocking reaction and can reduce the assay time by around 30 seconds, preferably by around 1 minute. In this embodiment, the blocking reagent will typically be included in the dilution mixture added at step i), or may alternatively be added after dilution, either before cell separation or after that cell separation process. In any case, if the blocking reagent can be added earlier than previously then assay time can be saved.

It is important in multi-analyte (panel) assays that where the blocking reagent is added before the sample is divided into portions for specific reaction, the blocking reagent should not interfere with detection of the various analytes. Where then analytes are HDL-CH, total-CH and total-TG, for example, the blocking reagent may be added at any of steps i) to iii) without intereference because the reagent causes blocking of non-HDL-CH (the second component) and thus allows specific reaction of HDL-CH. With regard to the total-CH and total-TG, although the blocking reagent will be present, the reagent mixture for specific reaction of these need only contain a suitable surfactant to release the total CH or total TG in spite of the block. Such surfactants will be known and easily selected by the skilled worker and so no interference with total-CH or total TG need take place.

In the kits of the present invention, the first reagent mixture is preferably formulated together with the first reagent mixture of the HDL reaction as a single reagent mixture. This reduces the number of steps, and thus reduces the assay time, and furthermore reduces the reagent storage and handling demands on the assay equipment, allowing the method to be practiced with less sophisticated automatic analysers.

The kit may additionally contain a lysing agent to cause cell lysis allowing determining the hematocrit.

DESCRIPTION OF THE DRAWINGS

The invention will now be further illustrated by the following non-limiting examples, and the attached Figures, in which:

FIG. 1 demonstrates that the estimated, non-measurable end point of HDL associated cholesterol in the presence of cholesterol associated with nonHDL coincides with the measurable end-point of the same amount of HDL associated cholesterol in the absence of cholesterol associated with nonHDL.

FIG. 2 compares end-point, fix-point and estimated end-point measurements in the Roche TG assay and shows that whereas fix-point measurements are strongly dependent upon reagent storage time, end-point and estimated end-point measurements are not.

FIG. 3 demonstrates the usefulness of end-point estimation in the measurement of HDL using a commercial HDL reagent. Estimated end-points correlated excellently with the determined HDL-levels.

FIG. 4 compares the HDL levels obtained by the estimated end-point method in an Afinion point-of-care instrument with those obtained by a clinical laboratory method. The figure gives a comparison of HDL levels determined by Afinion method and laboratory method using each of the "1st order" and the "Logistic" fitting algorithms.

FIG. 5 compares the HDL levels obtained by the estimated end-point method in an Afinion point-of-care instrument with those obtained by a commercial point-of-care method. The figure shows a comparison of HDL levels determined by the Afinion method and a comparative commercial point of care method. The fit is noticably poorer than for embodiments of the current invention (FIG. 4).

FIG. 6 demonstrates that the nonHDL blocking buffer, needed in the HDL assay, may be used as a general dilution buffer. The TG levels obtained in an Afinion point-of-care instrument, using blocking buffer as a dilution buffer, is compared with those obtained by a clinical laboratory method.

FIG. 7 compares the nonHDL levels obtained by the estimated end-point method in an Afinion point-of-care instrument with those obtained by a CRMLN certified laboratory.

FIG. 8 compares whole blood and plasma lipid profiles determined on an Afinion point-of-care analyzer.

EXAMPLES

Example 1

Estimation Of A Fictive End Measurement Of HdL Associated Cholesterol In The Presence Of Cholesterol Associated With Non-HdL.

A sample containing 66 mg/dL HDL, 255 mg/dL LDL and 300 mg/dL TG was analyzed on a Cobas Mira plus instrument (ABX Diagnostics) using Wako HDL-C L-type reagents and protocol (Table 4). The absorbance was monitored at 600 nm (FIG. 1, closed dots). A calibrator containing 64 mg/dL HDL but no significant amount of LDL was also analyzed in the same way (FIG. 1, open dots). The progress curves for the samples were close to identical for the first 200-300 s, but then diverged as the cholesterol of the non-HDL in the sample became unblocked and was being converted. The conversion of HDL associated cholesterol in the presence of cholesterol associated with other nonHDL thus has no measurable end-point. The only measurable end point will be that of the cholesterol present in HDL+ nonHDL (i.e. total cholesterol). However, from the first 200 s (thick line) of the progress curve of the sample, a fictive end-point for the HDL associated cholesterol could be computed (dotted line), using the first-order algorithm $$Y = Y\max(1 - e^{(-K(X-X0))}),$$

which coincided with the true end-point of a calibrator containing only HDL of almost the same concentration, 64 mg/dL versus 66 mg/dL. Other well known algorithms for following the kinetics of enzymatic reactions could be used in an analogous way.

TABLE 4

Wako HDL-C L-type reagent and protocol.

| R1 | Pretreatment | 5 minutes 37° C. |
|---|---|---|
| R2 | Incubation | 5 minutes 37° C. |
| R1 pretreatment | Good's buffer, pH 7.0 | 30 mmol/L |
| | 4-aminoantipyrine | 0.9 mmol/L |
| | peroxidase | 2400 U/L |
| | ascorbate oxidase | 2700 U/L |
| | anti-human β-lipoprotein antibody | |
| R2 enzyme reagent | Good's buffer, pH 7.0 | 30 mmol/L |
| | cholesterol esterase | 4000 U/L |
| | cholesterol oxidase | 20000 U/L |
| | F-DAOS | 0.8 mmol/L |

Example 2

Comparison Of End-Point, Fix-Point And Estimated End-Point Measurements In The TG Assay.

Roche TG reagent (Table 5) was stored at 25° C. and samples were taken out at different time points and used to measure a plasma sample containing 186 mg/dL triglyceride. The plasma sample was stored in aliquots frozen at −40° C. and thawed prior to measurement. The measurements were performed on a LabSystems Multiscan RC plate reader at ambient temperature (20-22° C.). The progress curves were followed until reaction completion and the end-points determined. In addition, the end-points were estimated based upon the first 300 s of the progress curves using a 4 parameter logistic function. The obtained estimated end-points were compared to true end-points and to the absorbance at the end of the time interval used for the estimation, 300 s. As seen in FIG. 2 estimated end-points followed true end-points whereas fix-point measurements were already falling off dramatically in comparison with the true end-points after as little as 5 months storage. Thus, while both end-point estimation and fixed-point methods allow a test period of only 300 seconds, fix-point measurements would need inclusion of calibrators to give correct values for the samples over any reasonable life span of the reagent. In contrast, estimated end-point computations would maintain accuracy without included calibrators.

TABLE 5

| Roche triglyceride GPO-PAP reagent | |
|---|---|
| buffer | Pipes 50 mmol/L, pH 6.8, containing 40 mmol/L Mg2+, sodium cholate 0.20 mmol/L, and 1 μmol/L potassium hexacyanoferrate (II) |
| ATP | 1.4 mmol/L |
| 4-aminoantipyrine | 0.13 mmol/L |
| 4-chlorophenol | 4.7 mmol/L |
| fatty alcohol polyglycol ether | 0.65% |
| lipoprotein lipase | 5000 U/L (from *Pseudomonas* spec.) |
| glycerokinase | 190 U/L (from *Bacillus stearothermoohilus*) |
| glycerol phosphate oxidase | 2500 U/L (from *E. coli*) |
| peroxidase | 100 U/L (from horseradish) |

Example 3

End-Point Estimation of the Roche HDL Assay

The HDL level of 8 different serum samples was determined on a 'Cobas Mira plus' instrument from ABX technologies using HDLC3 reagent from Roche (Table 6). Using the initial 100 seconds of the progress curves, fictive end-points were estimated using a 4-parameter logistic function. As shown in FIG. 3 the estimated end-points (in absorbance units) correlated excellently with the determined HDL levels.

TABLE 6

| Roche Direct HDLC3 reagents. | | |
|---|---|---|
| R1 | Pretreatment | 5 minutes 37° C. |
| R2 | Incubation | 5 minutes 37° C. |
| R1 pretreatment | Hepes, pH 7.4 | 10 mmol/L |
| | CHES, pH 7.4 | 97 mmol/L |
| | dextran sulfate | 1.5 g/L |
| | magnesium nitratehexahydrate | 12 mmol/L |
| | HSDA | 1 mmol/L |
| | Ascorbate oxidase (*Eupenicillium* sp) | 16.7 μkat/L |
| R2 enzyme reagent | Hepes, pH 7.0 | 10 mmol/L |
| | PEG-cholesterol esterase (*Pseudomonas* spec.) | 3.33 μkact/L |
| | PEG-cholesterol oxidase (*Streptomyces* spec.) | 127 μkat/L |
| | peroxidase (horseradish) | 333 μkat/L |
| | 4-aminoantipyrine | 2.5 mmol/L |

Example 4.

Example 4

The Afinion HDL Assay (Point-Of-Care)—Comparison to Large Clinical Instrument Assay Method.

The HDL levels of 49 scrum samples were determined on an Advia instrument and reagents from Siemens, the reference method. The samples also were measured by the estimated end-point method using Wako HDL-C L-type reagents (Table 4) on an Afinion point-of-care apparatus. Progress curves were monitored for 160 seconds and end-points estimated using two different algorithms: a $1^{st}$ order equation (Table 3, type 1) and a logistic equation (Table 3, type log-transformed). The estimated end-points were converted to concentrations using a calibration curves established on Afinion in a separate experiment using calibrators from Trina Bionostics, whose HDL levels had been determined on Cobas Mira plus using HDL direct CP reagents from ABX Pentra (Table 7). FIG. 4 shows for the 44 serum samples the correlation of the Afinion method with the reference method (1st order prediction—closed circles, logistic fitting, open circles). The mean HDL level as measured by the Afinion method was 0.4% (0.4 mg/dL) and 1.1% (0.6 mg/dL) lower compared to the reference method and the slope factor was 0.96 and 1.06 using $1^{st}$ order and logistic curve fitting, respectively.

TABLE 7

| ABX HDL Direct CP reagents. | | |
|---|---|---|
| R1 | Pretreatment | 5 minutes 37° C. |
| R2 | Incubation | 5 minutes 37° C. |
| R1 pretreatment | Good's buffer, pH 7.0 | |
| | cholesterol oxidase | 1000 U/L |
| | peroxidase | 1300 ppg U/L |
| | DSBmt | 1 mmol/L |
| | accelerator | 1 mmol/L |
| R2 enzyme reagent | Good's buffer, pH 7.0 | |
| | cholesterol esterase | 1500 U/L |
| | 4-aminoantipyrine | 1 mmol/L |
| | ascorbic acid oxidase | 3000 U/L |
| | detergent | 2% |
| | restrainer | 0.15% |

Example 5

The Afinion HDL Assay—Comparison to Point of Care Assay Method

The HDL level of 42 serum samples were determined on a point-of-care assay system from Cholestech, LDX system Lipid profile Glu. The samples also were measured and HDL values computed by the Afinion HDL method, essentially as described in Example 4. FIG. 5 shows for the 42 serum samples the correlation of the Afinion and LDX methods. As the LDX method reports HDL values below 15 mg/dL as <15mg/dL and values above 100 mg/dL as >100 mg/dL, these values (open circles) were omitted in the linear regression (n=10). The mean HDL level as measured by the Afinion was 1% (0.5 mg/dL) higher compared to the LDX method and the slope factor was 1.03.

Example 6

Correcting the Estimated End-Point of HDL in a Multi-Component Assay Method for Influence of Parallel Conversion Of NonHDL.

To exemplify the possibility of correcting the HDL assay for an influence of simultaneously converted nonHDL by postanalysis computations based upon concomitant measurement of totoal CH in the sample, the following experiment was performed:

(i) a calibration curve for HDL was constructed from a preparation of pure HDL (Wako High Unit HDL-C) using a Cobas Mira plus instrument and Wako HDL-C L-type reagents and protocol (Table 4). Estimated end-point absorbance from the first 300 s of the progress curves and curve fitting using a $1^{st}$ order function were used in the construction of the calibration curve:

$$HDL = 1.2 + 136.3 ABS \quad (1)$$

(ii) a calibration curve for the influence on the measured HDL value by a parallel conversion of nonHDL was constructed from mixtures of pure HDL and pure LDL (Wako High Unit LDL-C), two different concentrations of HDL and 4 different concentrations of LDL. The increase in the HDL measured was plotted as a function of the nonHDL concentration. The increase was exponentially correlated to the nonHDL concentration $$\text{HDL increase}=2.433 \exp\hat{\ }0.008499 \text{nonHDL} \quad (2)$$

The concentration of nonHDL was calculated from the difference between CH (total cholesterol measured) and HDL:

$$\text{nonHDL}=\text{CH}-\text{HDL} \quad (3)$$

A serum sample containing 111 mg/dL HDL was mixed at two different concentrations with different amounts of pure LDL. The CH and HDL levels were measured on a Cobas Mira plus instrument with ABX Pentra Cholesterol CP and the Wako HDL-C L-type reagents and protocol, respectively.

Measured values were on average 48% overestimated. After iterative correction using the equations (1) to (3) above the mean overestimation was decreased to 5% (Table 8).

TABLE 8

Influence of nonHDL on HDL measurement and correction thereof.

| Sample | CH | HDL true | HDL measured | HDL postanalysis corr |
|---|---|---|---|---|
| 36-1 | 117 | 36 | 41 | 36 |
| 36-2 | 231 | 36 | 52 | 40 |
| 36-3 | 336 | 36 | 68 | 38 |
| 62-1 | 204 | 62 | 70 | 62 |
| 62-2 | 314 | 62 | 84 | 64 |
| 62-3 | 428 | 62 | 120 | 69 |
| Grand mean | | 49 | 72.5 | 51.5 |

Samples were run in 2-3 replicates.

Example 7

Elimination of Cell Lysis by Blocking Reagent

20 µL of whole blood was added to 400 µL of HDL-C L-type R1 (Wako) added 0, 60, 90 or 120 mmol/L of NaCl. After mixing the absorbance of the samples were measured at 660 nm. At this wavelength there is no absorption from hemoglobin but strong interference (through scattering of light) from intact cells. While R1 added no NaCl caused almost complete lysis, R1 added 120 mmol/L NaCl caused insignificant cell lysis.

| NaCl added (mmol/L) | Absorption at 660 nm (AU) | Hemolysis (%) |
|---|---|---|
| 0 | 0.062 | 100 |
| 60 | 1.306 | 23 |
| 90 | 1.569 | 7 |
| 120 | 1.615 | 4 |

As can be seen, reduction of cell lysis to below 5% is achievable by appropriate choice of ionic strength in reagent R1.

Example 8

Use of Blocking Reagent Comprised Within Non-Lytic Dilution Buffer

Effect of using HDL reagent R1 as general dilution buffer on measurement of triglycerides.

The TG levels of 46 serum samples were determined on Afinion point-of-care instrument using HDL reagent R1 (Table) as the general dilution buffer and Roche TG reagent (Table 5).

15 µL sample was diluted into 280 µL of HDL reagent R1 and 58 µL was transferred to 100 µL of TG reagent. Reaction end-points were determined and converted to concentrations using a calibration curve established on Afinion in a separate experiment using calibrators that had been previously quantified at a CRMLN laboratory (Seattle, USA). In a parallel experiment the same samples were determined in a separate laboratory (Fürst Medical Laboratory, Oslo, Norway) using an Advia instrument and Siemens reagents. The samples compared very well between the two methods and there was no indication of a significant interference from the HDL R1 dilution buffer on the Afinion TG results (FIG. 6).

Table Dilution buffer

Dilution buffer Good's buffer, pH 7.0

NaCl 175 mmol/L 4-aminoantipyrine 0.9 mmol/L peroxidase 2400 U/L

Ascorbate oxidase 2700 U/L

Anti-human apo-β-lipoprotein antibody

Example 9

Dilution of Whole Blood in Isotonic HDL R1 and Filtration to Obtain an Essentially Cell Free Filtrate The applicability of HDL R1 (non-HDL blocking) reagent as a general dilution and filtration buffer for whole blood was investigated in an Afinion instrument supplied with filtration capability by placing a filter pad at the bottom of well nr.2. The dilution/filtration buffer was HDL-C L-type reagent 1 (R1) (Table 4) made nonlytic by adding NaCl to 175 mM.

Whole blood was drawn into a 15 µL sample device by capillary forces and inserted into the Multiwell cartridge which was placed in the instrument. The sample was emptied and mixed into 250 µL of the modified HDL R1, and the entire volume transferred into the well containing the filter pad. The membrane tube of the Multiwell cartridge was then positioned tightly over the filter pad. When below ambient pressure was applied to the open end of the membrane tube the diluted whole blood flowed into the filter pad and whereas blood cells were trapped in the filter, the diluted plasma flowed through the filter and into the membrane tube. When pressure started rising (sucking air) the membrane tube was removed from the filter, lowered into an empty well and forced to release the filtered plasma by applying an above ambient pressure. Blood contamination was measured after converting contaminating haemoglobin to methhemoglobin using $NaNO_2$ and measuring the absorbance at a wavelength of 410 nm. The absorbance was converted to %Hb by interpolation from a calibration curve constructed from known concentrations of methhemoglobin. Results given in Table 9 are the compounded results of hemolysis caused by dilution into the R1 reagent, hemolysis caused by filtration, and contamination by blood cells, not trapped in the filter pad.

TABLE 9

Total haemoglobin contamination after dilution into R1 and filtration.

| Filtertype | Whole blood % hematocrit | Filtrate % Hb contamination |
|---|---|---|
| Whatman | 37 | 0.9 |
| Whatman | 61 | 1.2 |
| Millipore AP25 | 37 | 0.5 |
| Millipore AP25 | 61 | 1.5 |
| Millipore 2 | 37 | 0.8 |
| Millipore 2 | 61 | 1.2 |

Mean of 5-6 replicates

Example 10

Estimation of a Fictive End Measurement of NonHDL Associated Cholesterol in the Presence of Cholesterol Associated with HDL. Comparison to Certified Laboratory Method.

A method for the direct determination of nonHDL was constructed by using a HDL specific block polymer that protects HDL while cholesterol associated with all other lipoproteins (nonHDL) are converted to a detectable product (HDL-X; Wako, Japan). As source for the HDL specific block polymer was used Reagent 1 from the Wako HDL-C L-M/2-PM reagent (Wako, Japan). The exact composition of Reagent 1 is not available, but it is disclosed to contain Good's buffer pH 7.0, cholesterol esterase, cholesterol oxidase, HMMPS, catalase, ascorbate oxidase and HDL blockpolymer. By supplementing Reagent 1 with peroxidise (6000 U/L), 4-aminoantipurin (0.8 mmol/L) and sodium azide (0.025%) a reagent was formulated that converted nonHDL into a detectable product while HDL was temporarily protected.

2 µL of calibrator or plasma sample was mixed with 150 µL of supplemented Reagent 1. The reaction was performed at 37C and monitored at 600 nm using a Cobas Mira plus instrument. End-point absorbance was estimated from the first 300 s of the progress curve using a 4 parameter logistic function (Table 3).

Calibrators and samples had been previously quantified at a CRMLN laboratory (Seattle, USA) with respect to CH, HDL and TG. From these values nonHDL values were calculated according to nonHDL=CH−HDL.

The nonHDL values of the 9 serum samples determined by the method of the invention correlated very well with the nonHDL values computed from the CRMLN values (FIG. 7)

Example 11

Whole Blood and Plasma Lipid Profiles Determined on an Afinion Point-of-Care Analyzer.

The plasma levels of CH, TG and HDL were determined on 15 µL of fresh whole blood obtained from 60 healthy volunteers, using an Afinion analyzer. From these data the LDL levels were computed in mg/dL using the Friedewald equation, LDL=CH−(HDL+TG/5). The plasma fraction of the same samples were also obtained (by centrifuging at 1000 g for 10 minutes) and measured on the Minion for the same analytes. The reagents used were those described in Tables 4 (HDL), 5 (TG) and 10 (CH). Reaction end-points were determined for TG and CH. The unmeasurable endpoint of the HDL reaction was estimated using the first 100 s of the progress curve and curve fitting using a $1^{st}$ order function (Table 3). Whole blood hematocrit was determined as described in Example 9 and whole blood results were converted to plasma results by dividing each result with (1-hematocrit) using the hematocrit value obtained for each specific whole blood sample. FIG. 8 depicts for the 60 samples the correlation between the plasma levels obtained in whole blood and plasma.

TABLE 10

| Roche Chol2 reagent | |
|---|---|
| buffer | Pipes 225 mmol/L, pH 6.8, containing 10 mmol/L Mg2+ |
| sodium cholate | 0.6 mmol/L |
| 4-aminoantipyrine | 0.45 mmol/L |
| phenol | 12.6 mmol/L |
| fatty alchol polyglycol ether | 3% |
| cholesterol esterase | 1500 U/L (*Pseudomonas* spec.) |
| cholesterol oxidase | 450 U/L (*E. coli*) |
| peroxidase | 750 U/L (horseradish) |

The invention claimed is:

1. An enzymatic method not requiring a non-high density lipoprotein (HDL) calibration standard for measuring the concentration of cholesterol associated with a non-HDL component in the plasma portion of a blood-cell containing sample, wherein the sample contains both a non-HDL component and a HDL component, which also comprises cholesterol, said method comprising the steps of
   i) diluting the sample;
   ii) substantially removing blood cells to provide a substantially cell free sample;
   iii) contacting said sample with a blocking reagent for the HDL component such that access to cholesterol from said HDL component is temporarily blocked while cholesterol from the non-HDL component remains accessible to a cholesterol converting enzyme;
   iv) contacting said sample with at least one converting enzyme that reacts specifically with the cholesterol associated with the non-HDL and generates one or more detectable reaction product(s);
   v) monitoring said detectable reaction product or products;
   vi) relating an amount of said detectable product or products to the concentration of the cholesterol associated with the non-HDL component in said blood sample, wherein the concentration of the cholesterol associated with said non-HDL component is related to the amount of said corresponding detectable reaction product or products by means of estimating an unmeasurable (fictive) endpoint for the concentration of the non-HDL- associated cholesterol by an algorithm; wherein step iii) may be carried out at any stage up to and including step iv) but before steps v) or vi) and wherein the blocking reagent of step iii) may be applied to the sample separately or in step i) or step iv) and wherein steps i) and iii) are carried out before step ii).

2. The method as claimed in claim 1 wherein the HDL component and the non-HDL component comprise a common lipid constituent but have different protein constituents.

3. The method as claimed in claim 1, wherein said non-HDL is LDL cholesterol.

4. The method as claimed in claim 1 wherein the blood cell containing sample is a whole blood sample.

5. The method of claim 1 wherein steps i) and iii) are carried out simultaneously.

6. The method as claimed in claim 1 wherein said non-HDL is a lipoprotein having a lipid constituent and a protein constituent and said HDL comprises the same lipid constituent associated with proteins other than said protein constituent of said non-HDL.

7. The method as claimed in claim 1 wherein the presence or generation of said blocked HDL in step iii) does not interfere with the reaction of any of said analytes or analyte constituents in step iv).

8. The method as claimed in claim 1 wherein said detectable products are detectable photometrically.

9. The method as claimed in claim 1 wherein the dilution of the blood sample is at least 10-fold.

10. The method as claimed in claim 1 wherein said substantially cell-free sample contains less than 5% blood cells.

11. The method as claimed in claim 1 wherein step ii) is carried out by filtration.

12. The method as claimed in claim 1 wherein step ii) is carried out without substantially causing cell lysis.

13. The method as claimed in claim 1 wherein step ii) is carried out without substantially affecting plasma lipid components.

14. The method as claimed in claim 1 wherein said at least one reagent which serves to block temporarily reaction of said HDL comprises a block polymer specific for said HDL over said non-HDL.

15. The method as claimed in claim 1 wherein the converting enzyme reacts with the cholesterol from the unblocked non-HDL component and starts to react with the cholesterol from the HDL component as the effect of the blocking agent diminishes.

16. The method of claim 1 requiring no more than 20 μL of blood.

17. The method as claimed in claim 1 wherein said algorithm is a first order rate equation or logistic function.

18. The method as claimed in claim 1 wherein said un-measurable endpoint cannot be measured because of an actual or potential unblocking of said blocked HDL component.

19. The method as claimed in claim 1, further comprising the measurement of a plurality of analytes.

20. The method of claim 1 wherein step ii) is carried out by causing lysis of no more than 5% of blood cells.

21. The method of claim 1 wherein step ii) is carried out by decreasing any of said components by not more than 5%.

22. The method of claim 1 wherein measuring cholesterol associated with non-HDL is one measurement of a plurality of measurements of lipid constituents of the sample.

23. The method of claim 8 wherein the concentration of cholesterol associated with non-HDL is related to the formation or consumption of a corresponding detectable product by estimating the endpoint, and wherein the endpoint is an unmeasurable (fictive) endpoint.

24. The method of claim 14 wherein the block polymer has binding specificity for a lipoprotein constituent of said HDL component.

* * * * *